US012061200B2

(12) United States Patent
Ruan et al.

(10) Patent No.: US 12,061,200 B2
(45) Date of Patent: Aug. 13, 2024

(54) DIRECT DETECTION OF SINGLE MOLECULES ON MICROPARTICLES

(71) Applicant: Abbott Laboratories, Abbott Park, IL (US)

(72) Inventors: Qiaoqiao Ruan, Abbott Park, IL (US); Patrick J. Macdonald, Abbott Park, IL (US); Kerry M. Swift, Abbott Park, IL (US); Sergey Y. Tetin, Abbott Park, IL (US); Brenda Calfin, Abbott Park, IL (US); Zhen Lin, Abbott Park, IL (US); Richard Haack, Abbott Park, IL (US); Mark R. Pope, Abbott Park, IL (US); John Prostko, Abbott Park, IL (US); Xiaoxing Qiu, Abbott Park, IL (US); M. Felicia Bogdan, Abbott Park, IL (US)

(73) Assignee: ABBOTT LABORATORIES, Abbott Park, IL (US)

(*) Notice: Subject to any disclaimer, the term of this patent is extended or adjusted under 35 U.S.C. 154(b) by 828 days.

(21) Appl. No.: 16/729,067

(22) Filed: Dec. 27, 2019

(65) Prior Publication Data

US 2020/0209250 A1 Jul. 2, 2020

Related U.S. Application Data

(60) Provisional application No. 62/785,798, filed on Dec. 28, 2018, provisional application No. 62/785,796, filed on Dec. 28, 2018.

(51) Int. Cl.
| | |
|---|---|
| *G01N 33/53* | (2006.01) |
| *G01N 15/14* | (2006.01) |
| *G01N 33/543* | (2006.01) |
| *G01N 33/58* | (2006.01) |
| *G01N 15/10* | (2006.01) |

(52) U.S. Cl.
CPC .......... *G01N 33/582* (2013.01); *G01N 15/14* (2013.01); *G01N 33/54346* (2013.01); *G01N 33/587* (2013.01); *G01N 2015/1018* (2013.01)

(58) Field of Classification Search
None
See application file for complete search history.

(56) References Cited

U.S. PATENT DOCUMENTS

| | | | |
|---|---|---|---|
| 4,778,751 A | 10/1988 | El Shami et al. | |
| 5,216,130 A | 6/1993 | Line et al. | |
| 5,480,792 A | 1/1996 | Buechler et al. | |
| 5,525,524 A | 6/1996 | Buechler et al. | |
| 5,583,054 A * | 12/1996 | Ito | G01N 33/54333 436/526 |
| 5,620,850 A | 4/1997 | Bamdad et al. | |
| 5,650,334 A * | 7/1997 | Zuk | G01N 33/533 436/523 |
| 5,679,526 A | 10/1997 | Buechler et al. | |
| 5,824,799 A | 10/1998 | Buechler et al. | |
| 5,837,475 A | 11/1998 | Dorsel et al. | |
| 5,851,776 A | 12/1998 | Valkirs | |
| 5,885,527 A | 3/1999 | Buechler | |
| 5,922,615 A | 7/1999 | Nowakowski et al. | |
| 5,939,272 A | 8/1999 | Buechler et al. | |
| 5,945,679 A | 8/1999 | Dorsel et al. | |
| 5,947,124 A | 9/1999 | Buechler et al. | |
| 5,985,579 A | 11/1999 | Buechler et al. | |
| 6,019,944 A | 2/2000 | Buechler | |
| 6,113,855 A | 9/2000 | Buechler | |
| 6,143,576 A | 11/2000 | Buechler | |
| 6,252,053 B1 | 6/2001 | Ohbayashi et al. | |
| 7,070,921 B2 | 7/2006 | Huang et al. | |
| 8,287,808 B2 | 10/2012 | Krupenkin et al. | |
| 9,239,284 B2 | 1/2016 | Livingston | |
| 2003/0232386 A1 | 12/2003 | Shah et al. | |
| 2006/0121544 A1 | 6/2006 | Boge et al. | |
| 2006/0205090 A1* | 9/2006 | Newton | G01N 33/5438 436/518 |
| 2007/0298435 A1 | 12/2007 | Aoyagi et al. | |

(Continued)

FOREIGN PATENT DOCUMENTS

| | | |
|---|---|---|
| EP | 1780545 B1 | 9/2010 |
| EP | 2765424 | 8/2014 |

(Continued)

OTHER PUBLICATIONS

Morimoto et al., Dextran as a generally applicable multivalent scaffold for improving immunoglobulin-binding affinities of peptide and peptidomimetic ligands, Bioconjugate Chemistry, 2014, 25, pp. 1479-1491. (Year: 2014).*
International Search Report and Written Opinion for PCT/US2019/068801. dated Mar. 27, 2020. 16 pages.
Abassi et al., Dendrimers: synthesis, applications, and properties. Nanoscale Res Lett. May 21, 2014;9(1):247. 10 pages.
Adamczyk et al., Homogeneous chemiluminescent assays for free choline in human plasma and whole blood. Anal Chim Acta. Oct. 2, 2006;579(1):61-7.
Banta et al., Replacing antibodies: engineering new binding proteins. Annu Rev Biomed Eng. 2013;15:93-113.

(Continued)

*Primary Examiner* — Gary Counts
(74) *Attorney, Agent, or Firm* — Casimir Jones SC; Lisa Mueller

(57) ABSTRACT

The disclosure provides methods of analyzing an analyte of interest in a biological sample using fluorescent agents and macroconjugates which comprise a core containing a crosslinked polymer or protein, tags, specific binding members or fragments thereof, and optionally carrier proteins. Also provided are methods of analyzing two or more analytes of interest in a biological sample in a single assay using microparticles and detection conjugates comprising different fluorophore labels, acquiring transmitted light and fluorescent images of the microparticles, and using a customized image analysis process to analyze the acquired images.

19 Claims, 18 Drawing Sheets

(56) References Cited

U.S. PATENT DOCUMENTS

| | | | |
|---|---|---|---|
| 2008/0052009 A1* | 2/2008 | Chiu | G01N 21/6428 702/21 |
| 2012/0308997 A1 | 12/2012 | Ruan et al. | |
| 2014/0274778 A1 | 9/2014 | Tsao et al. | |
| 2017/0153248 A1 | 6/2017 | Goix et al. | |
| 2018/0017552 A1 | 1/2018 | Duffy et al. | |

FOREIGN PATENT DOCUMENTS

| | | | |
|---|---|---|---|
| JP | 2001013145 A | | 1/2001 |
| JP | 2001305139 A | | 10/2001 |
| JP | 2002027990 A | | 1/2002 |
| JP | 2002521693 A | | 7/2002 |
| JP | 2003194821 A | | 7/2003 |
| JP | 2004510160 A | | 4/2004 |
| JP | 2018511805 A | | 4/2018 |
| WO | WO 97/17611 | | 5/1997 |
| WO | 2000007019 A1 | | 2/2000 |
| WO | WO 2007/136386 | | 11/2007 |
| WO | WO 2009/111431 | | 9/2009 |
| WO | WO 2010/040227 | | 4/2010 |
| WO | WO 2011/137533 | | 11/2011 |
| WO | WO 2013/066441 | | 5/2013 |
| WO | WO 2014/062551 | | 4/2014 |
| WO | WO 2014/066704 | | 5/2014 |
| WO | WO 2016/161400 | | 10/2016 |
| WO | WO 2016/161402 | | 10/2016 |
| WO | WO 2017/004463 | | 1/2017 |
| WO | 2018143478 A1 | | 8/2018 |

OTHER PUBLICATIONS

Béhar et al., Tolerance of the archaeal Sac7d scaffold protein to alternative library designs: characterization of anti-immunoglobulin G Affitins. Protein Eng Des Sel. Apr. 2013;26(4):267-75.

Capitanio et al., Interrogating biology with force: single molecule high-resolution measurements with optical tweezers. Biophys J. Sep. 17, 2013;105(6):1293-303.

Esfand et al., Poly(amidoamine) (PAMAM) dendrimers: from biomimicry to drug delivery and biomedical applications. Drug Discov Today. Apr. 1, 2001;6(8):427-436.

Fu et al., Dendrimer/DNA complexes encapsulated functional biodegradable polymer for substrate-mediated gene delivery. J Gene Med. Dec. 2008;10(12):1334-42.

Fu et al., Dendrimer/DNA complexes encapsulated in a water soluble polymer and supported on fast degrading star poly( DL-lactide) for localized gene delivery. Journal of Controlled Release. 2007. 124(3). 181-188.

Gilbreth et al., Structural insights for engineering binding proteins based on non-antibody scaffolds. Curr Opin Struct Biol. Aug. 2012;22(4):413-20.

Gottlin et al., Isolation of novel EGFR-specific VHH domains. J Biomol Screen. Jan. 2009;14(1):77-85.

Haugland, Handbook of Fluorescent Probes and Research Chemicals. Molecular Probes, Inc., Eugene, Oregon. 1996. TOC only. 4 pages.

Heller. Electrical wiring of redox enzymes. Acc. Chem. Res. 1990, 23, 5, 128-134.

Hermanson. (ed.), Bioconjugate Techniques, 3rd Edition, Academic Press. 2013. TOC only. 11 pages.

Holt et al., Domain antibodies: proteins for therapy. Trends Biotechnol. Nov. 2003;21(11):484-90.

Huang et al., Digital Microfluidic Dynamic Culture of Mammalian Embryos on an Electrowetting on Dielectric (EWOD) Chip. PLoS One. May 1, 2015;10(5):e0124196. 15 pages.

Jain et al., Probing cellular protein complexes using single-molecule pull-down. Nature. May 26, 2011;473(7348):484-8.

Jain et al., Single-molecule pull-down for studying protein interactions. Nat Protoc. Feb. 9, 2012;7(3):445-52.

Keller et al., Complex RNA folding kinetics revealed by single-molecule FRET and hidden Markov models. J Am Chem Soc. Mar. 26, 2014;136(12):4534-43.

Kobitski et al., Mg2+-dependent folding of a Diels-Alderase ribozyme probed by single-molecule FRET analysis. Nucleic Acids Res. 2007;35(6):2047-59.

Kukalkar et al., Single-molecule total internal reflection fluorescence microscopy. Cold Spring Harbor Protocols. 2016.(5), pdb. top077800. 5 pages.

Lang et al., An automated two-dimensional optical force clamp for single molecule studies. Biophys J. Jul. 2002;83(1):491-501.

Lee et al., Real-time single-molecule coimmunoprecipitation of weak protein-protein interactions. Nat Protoc. Oct. 2013;8(10):2045-60.

Marquette et al., Recent advances in multiplex immunoassays. Bioanalysis. May 2012;4(8):927-36.

Mattson et al., A practical approach to crosslinking. Mol Biol Rep. Apr. 1993;17(3):167-83.

Mcenaney et al., Antibody-recruiting molecules: an emerging paradigm for engaging immune function in treating human disease. ACS Chem Biol. Jul. 20, 2012;7(7):1139-51.

Millward et al., Iterative in situ click chemistry assembles a branched capture agent and allosteric inhibitor for Akt1. J Am Chem Soc. Nov. 16, 2011;133(45):18280-8.

Min et al., Observation of a power-law memory kernel for fluctuations within a single protein molecule. Phys Rev Lett. May 20, 2005;94(19):198302. 4 pages.

Oliner. (ed), Acoustic Surface Waves. Springer. 1978. TOC only. 8 pages.

Patel et al., Selection of a high-affinity WW domain against the extracellular region of VEGF receptor isoform-2 from a combinatorial library using CIS display. Protein Eng Des Sel. Apr. 2013;26(4):307-15.

Peng et al., EWOD (electrowetting on dielectric) digital microfluidics powered by finger actuation. Lab Chip. Mar. 21, 2014;14(6):1117-22.

Polak et al., Introduction to Immunocytochemistry, 3rd ed., Springer Verlag, N.Y. 2003. TOC only. 10 pages.

Rader. Chemically programmed antibodies. Trends Biotechnol. Apr. 2014;32(4):186-97.

Reck-Peterson et al., Imaging single molecules using total internal reflection fluorescence microscopy (TIRFM). Cold Spring Harb Protoc. Mar. 2010;2010(3):pdb.top73. 12 pages.

Ruan et al., Imaging single molecules vs. single-molecules using Dextran-Streptavidin-Antibody clusters (DSA). Biophysical Journal. 2017. 112(3), 295a.

Sako et al., Single-molecule imaging of EGFR signalling on the surface of living cells. Nat Cell Biol. Mar. 2000;2(3):168-72.

Skinner et al., Rapid single-molecule imaging in cyclic olefin copolymer channels. Microsc Res Tech. Apr. 2015;78(4):309-16.

Tiede et al., Adhiron: a stable and versatile peptide display scaffold for molecular recognition applications. Protein Eng Des Sel. May 2014;27(5):145-55.

Yang et al., Protein conformational dynamics probed by single-molecule electron transfer. Science. Oct. 10, 2003;302(5643):262-6.

Yildiz et al., Myosin V walks hand-over-hand: single fluorophore imaging with 1.5-nm localization. Science. Jun. 27, 2003;300(5628):2061-5.

Green S, et al. Partial purification of a serum factor that causes necrosis of tumors. Proc Natl Acad Sci U S A. Feb. 1976;73(2):381-5.

Gust, Alexander et al., A Starting Point for Fluorescence-Based Single-Molecule Measurements in Biomolecular Research, molecules, Sep. 30, 2014, vol. 19, p. 15824-15865.

Diamandis et al., Immunoassay, Academic Press, Chapter 11, The Avidin-Biotin System, 237-255 (1996).

Ruan, Qiaoqiao et al. (2017). Imaging Single Molecules vs. Single-Molecule Imaging: Counting Single Molecules using Dextran-Streptavidin-Antibody Clusters (DSA). Biophysical Journal. 112. 2017. Issue 3, p. 295. 10.1016/j.bpj.2016.11.1599. (1450-Pos Board B518).

(56) References Cited

OTHER PUBLICATIONS

European Patent Office, Extended European Search Report for EP Application No. EP24167359.9 issued Jun. 20, 2024.

* cited by examiner

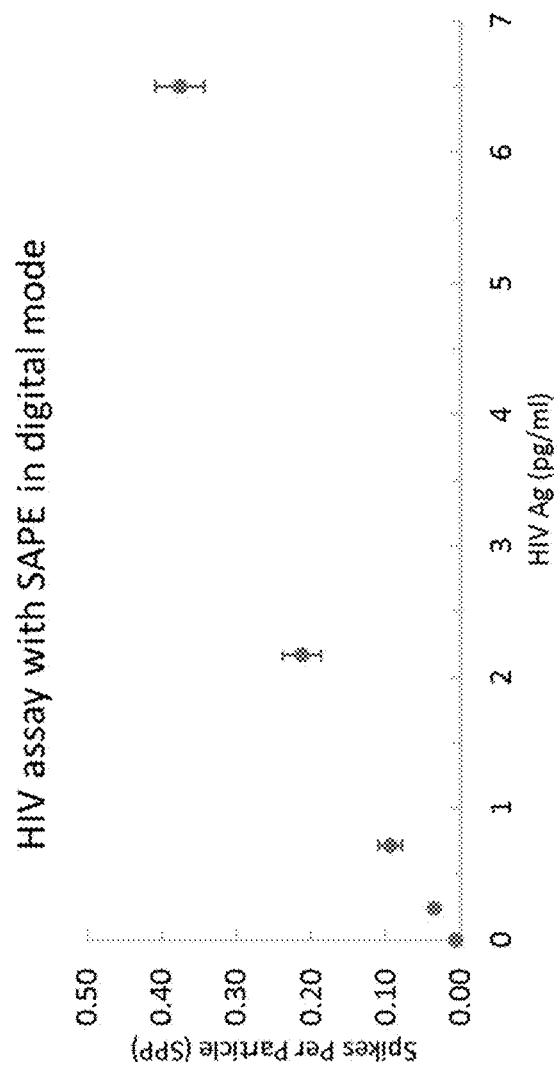

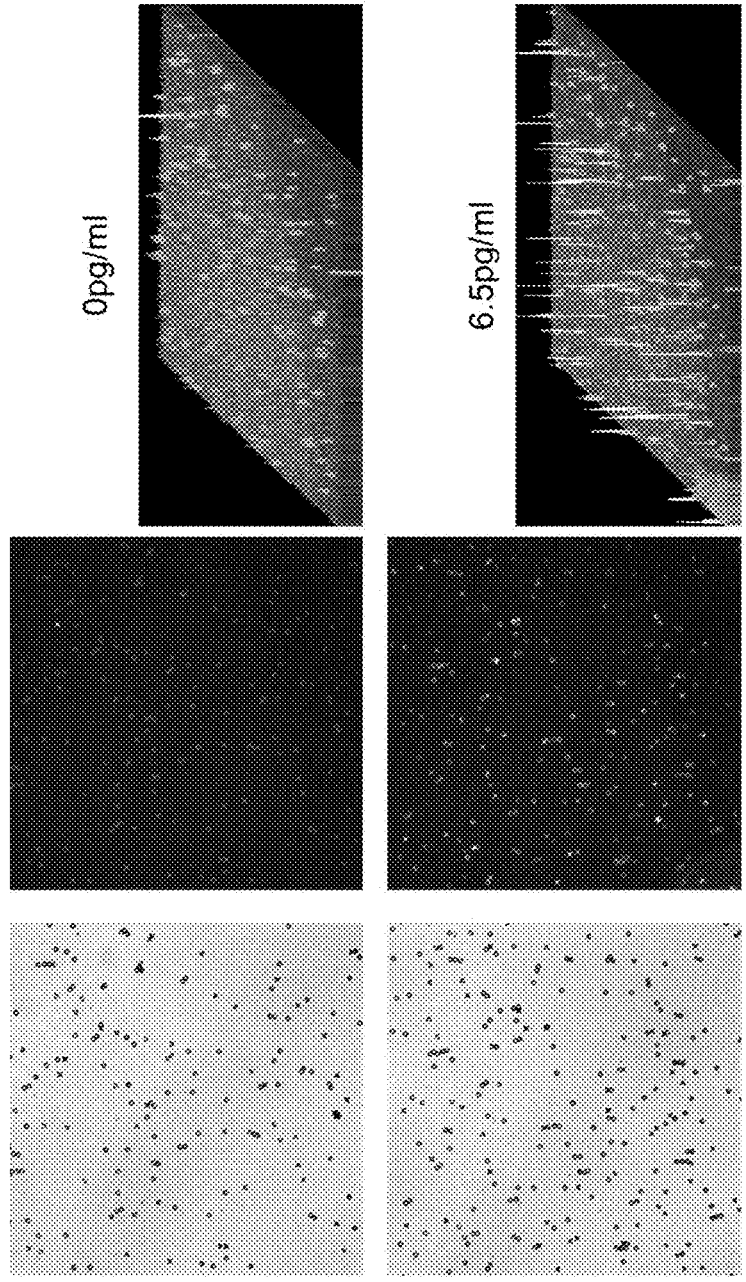

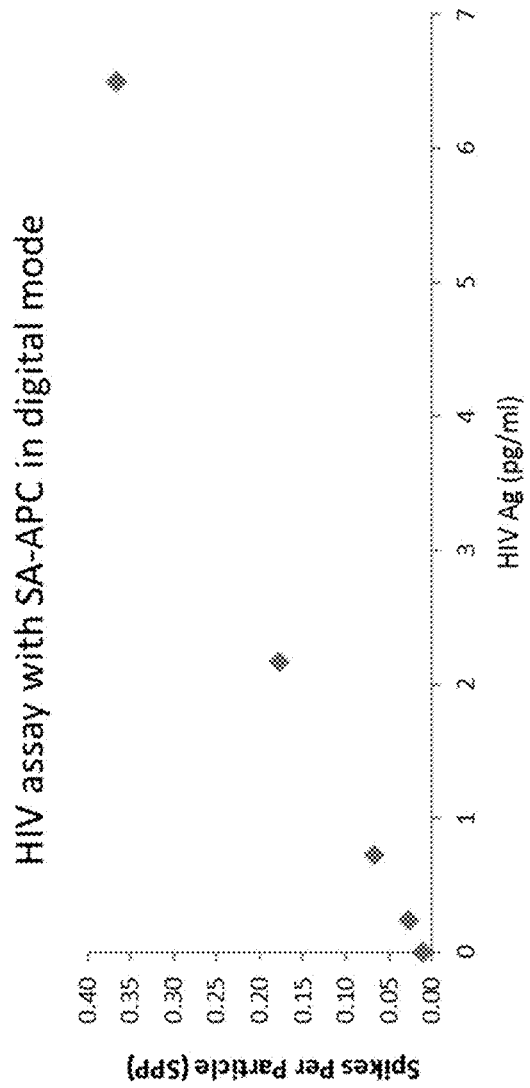

DIRECT DETECTION OF SINGLE MOLECULES ON MICROPARTICLES

CROSS-REFERENCE TO RELATED APPLICATIONS

This patent application claims the benefit of U.S. Provisional Patent Application No. 62/785,796, filed Dec. 28, 2018, and U.S. Provisional Patent Application No. 62/785,798, filed Dec. 28, 2018, both of which are incorporated by reference herein.

BACKGROUND

Conventional immunodiagnostic assays involve ensemble measurements, wherein target molecules are identified in a reaction vial by recording the cumulative signal. More recently, immunoassays have been developed which can count single analyte molecules, which are known in the art as "digital immunoassays." One such approach involves tagging a detection antibody with an enzyme and trapping individual microparticles in nanowells. It is assumed that at low sample concentration, a single analyte molecule, bound to the antibody-enzyme conjugate and captured by a microparticle confined in the nanowell, can convert enough substrate to a fluorescent state to become detectable in a reasonable timeframe. Empty nanowells, as well as nanowells with microparticles that didn't capture analyte and/or conjugate, remain dark. The essence of this approach depends on the presence of a large number of non-fluorescent, microparticle-containing wells in order to satisfy the rules of single-molecule counting statistics. These sensitive techniques also are frequently referred to in the art as Single-Molecule Enzyme-Linked Immuno-Sorbent Analysis (smELISA). However, they require additional steps and reagents, cumbersome detection devices, and are time consuming as compared to standard immunoassays. They are also less adaptable to transitioning between counting (digital) and averaging (analog) modalities, which reduces the detection dynamic range.

Another issue for immunodiagnostic assays is the ability to measure two or more analytes from one sample in a single assay, otherwise known as "multiplexing," is highly sought after within the in vitro diagnostic (IVD) field (Marquette et al., *Bioanalysis*, 4: 927-936 (2012)). Multiplex immunoassays offer greater throughput, reduced time per result, fewer consumables, and reduced costs as compared to singleplex immunoassays. However, reagent complexity, non-specific binding, and interference among the reagents may produce inaccurate results and low sensitivity in multiplex immunoassays. To address these issues, multiplex immunoassays have been developed that use multi-colored beads to distinguish individual analytes in a sample (e.g., LUMINEX® 100/200™ (Luminex Corp., Austin, TX). Many such multi-color bead formats, however, still suffer from less than optimal sensitivity and signal interference among the multiple analytes.

As such, there is a need for alternative methods and devices to perform highly-sensitive digital immunoassays over a wide dynamic range, as well as a need for multiplex immunoassay methods and systems with high sensitivity and low reagent interference.

BRIEF SUMMARY OF THE INVENTION

The disclosure provides a method of analyzing an analyte of interest in a biological sample, the method comprising the steps of: (a) capturing an analyte of interest on a binding surface, which binding surface comprises a plurality of specific binding members immobilized thereto that bind to the analyte; (b) reacting a plurality of macroconjugates with the captured analyte; wherein each macroconjugate comprises: (i) a core which comprises a cross-linked protein or polymer comprising a polysaccharide, a dendrimer, a polyether compound, or nanoparticle; (ii) a plurality of specific binding members, fragments thereof, or combinations thereof; (iii) a plurality of tags or detectable labels, wherein when the macroconjugate comprises a plurality of tags, the method comprises reacting a plurality of fluorescent agents with the tags, wherein each fluorescent agent comprises a molecule which is capable of binding to the tag and a detectable label; and optionally (iv) a plurality of carrier proteins; and (c) imaging the binding surface and analyzing the images.

Also provided is a method of analyzing an analyte of interest in a biological sample, the method comprising the steps of: (a) capturing an analyte of interest on a binding surface, which binding surface comprises a plurality of specific binding members immobilized thereto that bind to the analyte; (b) reacting a plurality of macroconjugates with the captured analyte; wherein each macroconjugate comprises: (i) a core which comprises a cross-linked protein or polymer comprising a polysaccharide, a dendrimer, a polyether compound, or nanoparticle; (ii) a plurality of carrier proteins covalently attached to locations around the core; (iii) a plurality of specific binding members, fragments thereof, or combinations thereof covalently attached to the carrier proteins; and (iv) a plurality of tags covalently attached to the plurality of carrier proteins or the plurality of specific binding members; (c) reacting a plurality of fluorescent agents with the macroconjugates, wherein each fluorescent agent comprises a molecule which is capable of binding to the tag and a detectable label; and (d) imaging the binding surface and analyzing the images.

The disclosure also provides a method of analyzing two or more analytes of interest in a biological sample in a single assay. The method comprises (a) capturing a first analyte of interest on a surface of a first microparticle, wherein the first microparticle (i) comprises a plurality of specific binding members immobilized on the surface thereof which bind to the first analyte and (ii) is labeled with a first fluorophore; (b) capturing a second analyte of interest on a surface of a second microparticle, wherein (i) the first analyte is different from the second analyte, and (ii) the second microparticle comprises a plurality of specific binding members immobilized on the surface thereof which bind to the second analyte; (c) reacting the captured first analyte of interest with a first conjugate, wherein the first conjugate comprises a specific binding member that is labeled with a second fluorophore and binds to the first analyte; (d) reacting the captured second analyte with a second conjugate, wherein the second conjugate comprises a specific binding member that is labeled with a third fluorophore and binds to the second analyte, and wherein the first, second, and third fluorophores are different; (e) obtaining a transmitted light image of the first and second microparticles; (f) obtaining separate fluorescent images of the first and second microparticles corresponding to the first, second, and third fluorophores, respectively; and (g) analyzing the images using a customized image analysis process.

The disclosure further provides a method of analyzing two or more analytes of interest in a biological sample in a single assay, which method comprises: (a) capturing a first analyte of interest on a surface of a first microparticle, wherein the first microparticle comprises a plurality of specific binding members immobilized on the surface thereof which bind to the first analyte; (b) capturing a second analyte of interest on a surface of a second microparticle, wherein (i) the first analyte is different from the second analyte, (ii) the second microparticle comprises a plurality of specific binding members immobilized on the surface thereof which bind to the second analyte, and (iii) the first microparticle and the second microparticles differ in size and/or shape; (c) reacting the captured first analyte of interest with a first conjugate, wherein the first conjugate comprises a specific binding member that comprises a first fluorophore and binds to the first analyte; (d) reacting the captured second analyte with a second conjugate, wherein the second conjugate comprises a specific binding member that comprises a second fluorophore and binds to the second analyte, and wherein the first and second fluorophores are different; (e) obtaining a transmitted light image of the first and second microparticles; (f) obtaining separate fluorescent images of the first and second microparticles corresponding to the first and second fluorophores, respectively; and (g) analyzing the images using a customized image analysis process.

BRIEF DESCRIPTION OF THE DRAWINGS

FIG. 4A is a graph which illustrates a calibration curve for the HIV P24 assay described in Example 3. FIG. 4B is a series of transmitted light images (left panels), fluorescent images (center panel), and intensity profiles (right panels) of the HIV P24 assay at 0 and 6.5 pg/ml.

FIG. 5 shows a calibration curve of the HIV P24 assay using SA-APC as the fluorescent agent, as described in Example 3.

DETAILED DESCRIPTION OF THE INVENTION

Figure 1:
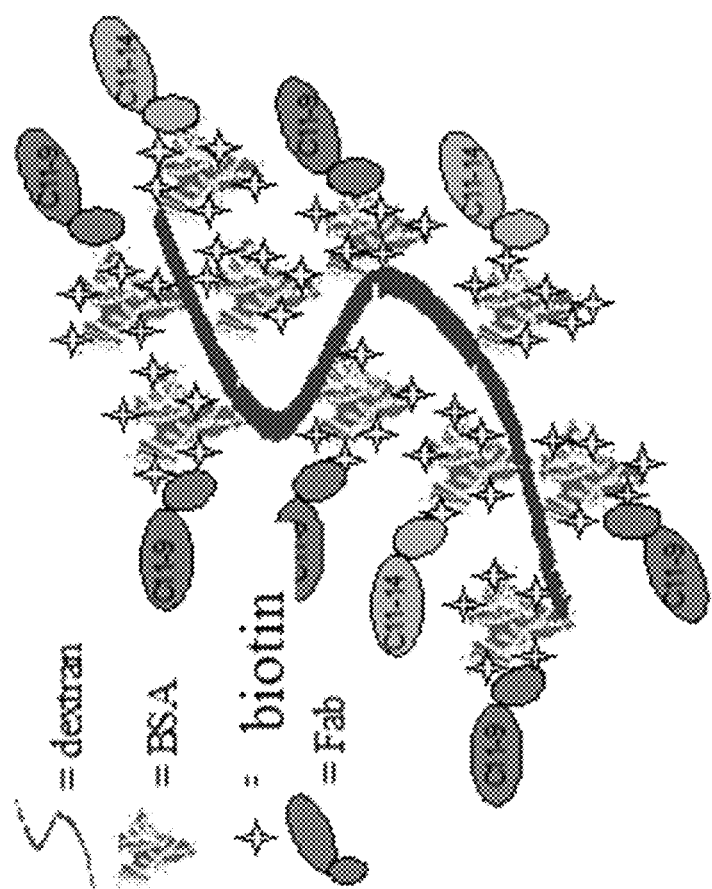
FIG. 1 is a diagram illustrating an exemplary macroconjugate, in which dextran is the cross-linked polymer, bovine serum albumin (BSA) is the carrier protein, biotin is the capture tag, and a plurality of Fabs are the antibody fragments.

The present disclosure is predicated, at least in part, on the discoveries that using macroconjugates and fluorescent agents in an immunoassay allows for direct visualization and analysis of a single immune complex without requiring enzyme amplification and nanowells, and that a single multiplex analyte assay using microparticles and detection conjugates comprising different fluorophore labels, combined with transmitted light and fluorescent image analysis, results in reduced interference among the analytes and reagents. The image analysis described herein also increases sensitivity of the multiplex assay as compared to other known methods that employ flow cytometry-based detection methods.

Definitions

To facilitate an understanding of the present technology, a number of terms and phrases are defined below. Additional definitions are set forth throughout the detailed description.

As used herein, the terms "biological sample," "sample," and "test sample" are used interchangeably and refer to a substance containing or suspected of containing an analyte of interest. The biological sample may be derived from any suitable source. For example, the source of the biological sample may be synthetic (e.g., produced in a laboratory), or a naturally-occurring substance obtained or derived from, e.g., the environment (e.g., air, soil, fluid samples, e.g., water supplies, etc.), an animal (e.g., a mammal), a plant, or another organism. In one embodiment, the source of the biological sample is a human bodily substance (e.g., bodily fluid, blood, serum, plasma, urine, saliva, sweat, sputum, semen, mucus, lacrimal fluid, lymph fluid, amniotic fluid, interstitial fluid, lung lavage, cerebrospinal fluid, feces, tissue, an organ, and the like). Human tissues may include, but are not limited to, skeletal muscle tissue, liver tissue, lung tissue, kidney tissue, myocardial tissue, brain tissue, bone marrow, cervix tissue, skin, and the like. In some embodiments, the source of the sample may be a biopsy sample, which may be solubilized by tissue disintegration/cell lysis. The sample may be a liquid sample, a liquid extract of a solid sample, a fluent particulate solid, or fluid suspension of solid particles.

The terms "analyte," "target analyte," and "analyte of interest" are used interchangeably herein and refer to the substance being measured in the disclosed method. Any analyte that can be specifically bound by a specific binding member may be detected, and optionally quantified, using the methods of the present disclosure.

The term "binding surface," as used herein, refers to any surface onto which a specific binding member (e.g., an antibody, as discussed herein) can be immobilized and analyte detection assays can be performed. Any suitable binding surface may be used in the context of the present disclosure. In some embodiments, the binding surface comprises a plurality of microparticles (e.g., 2 or more, 50 or more, 100 or more, 1,000 or more, or 5,000 or more).

The term "region of interest (ROI)," as used herein, refers to a region, for example, a set of pixels, in an image that are selected for further analysis. In an image, a region can be contiguous or non-contiguous. The terms "region of interest (ROI) area," "total area," or "total binding area" are used interchangeably herein to refer to the area of the selected region. When defining the region by pixels, the terms "region of interest area," "total area," or "total binding area" may also refer to the total number or sum of pixels in a region of interest.

The term "contacting," as used herein, refers to any type of combining action which brings a binding member into sufficiently close proximity with an analyte of interest in a sample such that a binding interaction will occur if the analyte of interest specific for the binding member is present in the sample.

The term "macroconjugate," as used herein, refers to a complex comprising two or more molecules that are specifically bound to one another. For example, a macroconjugate may comprise three or more (e.g., 4, 5, 6, 7, 8, 9, or 10 or more) molecules specifically bound to one another.

The terms "specific binding partner" and "specific binding member" are used interchangeably herein and refer to one of two or more different molecules that specifically recognize the other molecule compared to substantially less recognition of other molecules. The one of two different molecules has an area on the surface or in a cavity, which specifically binds to, and is thereby defined as complementary with, a particular spatial and polar organization of the other molecule. The molecules may be members of a specific binding pair. For example, a specific binding member may include, but is not limited to, a protein, such as a receptor, an enzyme, and an antibody.

The term "detectable label," as used herein, refers to a moiety that can produce a signal that is detectable by visual or instrumental means. The detectable label may be, for example, a signal-producing substance, such as a chromagen, a fluorescent compound, an enzyme, a chemiluminescent compound, a radioactive compound, etc. In one embodiment, the detectable label may be a fluorescent compound.

As used herein, the term "spatial information" refers to identification of a location from which a signal emanates.

The term "pixel," as used herein, refers to a single point in a digital image, or the smallest addressable screen element in a display device. A pixel is the smallest unit of picture that can be represented or controlled. Each pixel has its own address. The address of a pixel corresponds to its spatial coordinates. Pixels are usually arranged in a two-dimensional grid and are often represented using dots or squares. Each pixel is a sample of an original image; more samples typically provide more accurate representations of the original. The intensity of each pixel typically is variable, and the total number of pixels in an image can vary. A representative example of the number of pixels in a digital image is 1024×1024.

The term "intensity," as used herein, refers to the amount or degree of strength of electricity, light, heat, or sound per unit area or volume. More particularly, with respect to the methods described herein, the term "intensity" refers to the number of photons counted per unit of area per unit of time. For example, 1000 photons per unit area may be recorded as 500 counts in a single pixel, while 80 photons per unit area are recorded as 40 counts in a single pixel. The particular conversion depends on the camera system used. Intensity is proportional to the number of photons counted.

The term "photon," as used herein, refers to a particle representing a quantum of light or other electromagnetic radiation. A photon carries energy proportional to the radiation frequency but has zero rest mass.

The term "digital mode," as used herein, refers to a type of image analysis in which the region of interest area is identified and the total number of high intensity peaks (e.g., high intensity fluorescent peaks) on one or more binding surface(s) is counted. In some embodiments, the ratio of total number of high intensity peaks to region of interest area can be determined and expressed as "peaks per area" or "PPA." Each high intensity peak identified on the binding surface corresponds to a single immunosandwich complex. A peak may be a single pixel or a cluster of pixels which intensities are above a predefined threshold. The predetermined threshold chosen will depend upon, inter alia, the analyte of interest and the detectable label used.

The term "analog mode," as used herein, refers to a type of image analysis in which the total pixel intensity in a region of interest area is calculated in the one or more fluorescent images. If the signal value calculated in analog mode is below a preset value, then the fluorescent images may be analyzed in digital mode (i.e., analysis is switched from analog to digital mode). Digital and analog modes of analysis are illustrated schematically in FIG. 2.

The terms "mask" and "image mask" are used interchangeably herein to refer to a tool used to distinguish the portion of an image upon which further examination of specified features can be performed. Masks may spatially distinguish the area of an area of interest and exclude other areas of the image that might confound the analysis. For example, a mask may distinguish a particular immunosandwich and/or microparticle from background or non-specific fluorescence. Features of interest may be assigned the number "1" or the color white, while features not of interest may be assigned the number "0" or the color black.

The term "conversion factor," as used herein, refers to a coefficient that is used to combine the digital and analog portions of the calibration curve. It is calculated using the overlapping interval in which both the digital and the analog signals can be clearly determined. These conversion factors are assay specific and should be set when generating calibration curves.

Biological Sample

Any suitable volume of the sample may be provided. It will be appreciated that sensitive detection of rare targets requires large sample volumes, ranging from 100 μL to about 2 mL. For more abundant targets, single molecule (SM) detection methods can operate with smaller sample volumes. In this regard, the volume of the biological sample may be about 10 μl to about 50 μl (e.g., 10 μl, 15 μl, 20 μl, 25 μl, 30 μl, 35 μl, 40 μl, or 50 μl). In another embodiment, the volume of the biological sample may be about 10 μl to about 30 μl (e.g., 10 μl, 11 μl, 12 μl, 13 μl, 14 μl, 15 μl, 16 μl, 17 μl, 18 μl, 19 μl, 20 μl, 21 μl, 22 μl, 23 μl, 24 μl, 25 μl, 26 μl, 27 μl, 28 μl, 29 μl, 30 μl, or a range defined by any two of the foregoing values).

In some embodiments, a liquid biological sample may be diluted prior to use in an assay. For example, in embodiments where the biological sample is a human body fluid (e.g., blood or serum), the fluid may be diluted with an appropriate solvent (e.g., PBS buffer). A fluid sample may be diluted about 1-fold, about 2-fold, about 3-fold, about 4-fold, about 5-fold, about 6-fold, about 10-fold, about 100-fold, or greater, prior to use.

In other embodiments, the sample may undergo pre-analytical processing. Pre-analytical processing may offer additional functionality, such as nonspecific protein removal, analyte enrichment, and/or effective yet inexpensive implementable mixing functionality. General methods of pre-analytical processing include, for example, the use of electrokinetic trapping, AC electrokinetics, surface acoustic waves, isotachophoresis, dielectrophoresis, electrophoresis, and other pre-concentration techniques known in the art. In some cases, a liquid sample may be concentrated prior to use in an assay. For example, in embodiments where biological sample is a human body fluid (e.g., blood, serum), the fluid may be concentrated by precipitation, evaporation, filtration, centrifugation, or a combination thereof. A fluid sample may be concentrated about 1-fold, about 2-fold, about 3-fold, about 4-fold, about 5-fold, about 6-fold, about 10-fold, about 100-fold, or greater, prior to use.

Analytes

In some embodiments, the analyte may be a biomolecule. Examples of suitable biomolecules include, but are not limited to, macromolecules such as, proteins, lipids, and carbohydrates. Other biomolecules include, for example, hormones, antibodies, growth factors, oligonucleotides, polynucleotides, haptens, cytokines, enzymes, receptors (e.g., neural, hormonal, nutrient, and cell surface receptors) or their ligands, cancer markers (e.g., PSA, TNF-alpha), markers of myocardial infarction (e.g., BNP, troponin, creatine kinase, and the like), toxins, metabolic agents (e.g., vitamins), and the like. Suitable protein analytes include, for example, peptides, polypeptides, protein fragments, protein complexes, fusion proteins, recombinant proteins, phosphoproteins, glycoproteins, lipoproteins, and the like.

In certain embodiments, the analyte may be a post-translationally modified protein (e.g., phosphorylated, methylated, glycosylated protein) and the specific binding member may be an antibody specific to the post-translational modification. A modified protein may be bound to a specific binding member immobilized on a solid support where the specific binding member binds to the modified protein but not the unmodified protein.

A non-limiting list of analytes that may be analyzed by the methods disclosed herein include Aβ42 amyloid beta-protein, fetuin-A, tau, secretogranin II, prion protein, alpha-synuclein, tau protein, NSE, S100B, NF-L, ApoA1, BDNF, MBP, Sodium creatinine, BUN, AMPAR, prion protein, neurofilament light chain, parkin, PTEN induced putative kinase 1, DJ-1, leucine-rich repeat kinase 2, mutated ATP13A2, Apo H, ceruloplasmin, peroxisome proliferator-activated receptor gamma coactivator-1 alpha (PGC-1α), transthyretin, vitamin D-binding protein, proapoptotic kinase R (PKR) and its phosphorylated PKR (pPKR), CXCL13, IL-12p40, CXCL13, IL-8, Dkk-3 (semen), p14 endocan fragment, Serum, ACE2, autoantibody to CD25, hTERT, CAI25 (MUC 16), VEGF, sIL-2, osteopontin, human epididymis protein 4 (HE4), alpha-fetoprotein, albumin, albuminuria, microalbuminuria, neutrophil gelatinase-associated lipocalin (NGAL), interleukin 18 (IL-18), kidney injury molecule-1 (KIM-1), liver fatty acid binding protein (L-FABP), LMP1, BARF1, IL-8, carcinoembryonic antigen (CEA), BRAF, CCNI, EGRF, FGF19, FRS2, GREB1, LZTS1, alpha-amylase, carcinoembryonic antigen, CA 125, IL8, thioredoxin, beta-2 microglobulin, tumor necrosis factor-alpha receptors, CA15-3, follicle-stimulating hormone (FSH), leutinizing hormone (LH), T-cell lymphoma invasion and metastasis 1 (TIAM1), N-cadherin, EC39, amphiregulin, dUTPase, secretory gelsolin (pGSN), prostate specific antigen (PSA), thymosin β15, insulin, plasma C-peptide, glycosylated hemoglobin (HBA1c), C-Reactive Protein (CRP), Interleukin-6 (IL-6), Rho GDP-dissociation inhibitor 2 (ARHGDIB), cofilin-1 (CFL1), profilin-1 (PFN1), glutathione S-transferase P (GSTP1), protein S100-A11 (S100A11), peroxiredoxin-6 (PRDX6), 10 kDa heat shock protein, mitochondrial (HSPE1), lysozyme C precursor (LYZ), glucose-6-phosphate isomerase (GPI), histone H2A type 2-A (HIST2H2AA), glyceraldehyde-3-phosphate dehydrogenase(GAPDH), basement membrane-specific heparin sulfate proteoglycan core protein precursor (HSPG2), galectin-3-binding protein precursor (LGALS3BP), cathepsin D precursor (CTSD), apolipoprotein E precursor (APOE), Ras GTPase-activating-like protein (IQGAP1), ceruloplasmin precursor (CP), and IGLC2, PCDGF/GP88, EGFR, HER2, MUC4, IGF-IR, p27(kipl), Akt, HER3, HER4, PTEN, PIK3CA, SHIP, Grb2, Gab2, 3-phosphoinositide dependent protein kinase-1 (PDK-1), TSC1, TSC2, mTOR, ERBB receptor feedback inhibitor 1 (MIG-6), S6K, src, KRAS, mitogen-activated protein kinase 1 (MEK), cMYC, topoisomerase (DNA) II alpha 170 kDa, FRAP1, NRG1, ESR1, ESR2, PGR, CDKN1B, MAP2K1, NEDD4-1, FOXO3A, PPP1R1B, PXN, ELA2, CTNNB1, AR, EPHB2, KLF6, ANXA7, NKX3-1, PITX2, MKI67, PHLPP, adiponectin (ADIPOQ), fibrinogen alpha chain (FGA), leptin (LEP), advanced glycosylation end product-specific receptor (AGER or RAGE), alpha-2-HS-glycoprotein (AHSG), angiogenin (ANG), CD14, ferritin (FTH1), insulin-like growth factor binding protein 1 (IGFBP1), interleukin 2 receptor, alpha (IL2RA), vascular cell adhesion molecule 1 (VCAM1), Von Willebrand factor (VWF), myeloperoxidase (MPO), IL1α, TNFα, perinuclear anti-neutrophil cytoplasmic antibody (p-ANCA), lactoferrin, calprotectin, Wilm's Tumor-1 protein, Aquaporin-1, MLL3, AMBP, VDAC1, *E. coli* enterotoxins (heat-labile exotoxin, heat-stable enterotoxin), influenza HA antigen, tetanus toxin, diphtheria toxin, botulinum toxins, Shiga toxin, Shiga-like toxin I, Shiga-like toxin II, *Clostridium difficile* toxins A and B, drugs of abuse (e.g., cocaine), protein biomarkers (including, but not limited to, nucleolin, nuclear factor-kB essential modulator (NEMO), CD-30, protein tyrosine kinase 7 (PTK7), MUC1 glycoform, immunoglobulin µ heavy chains (IGHM), immunoglobulin E, $\alpha v \beta 3$ integrin, $\alpha$-thrombin, HIV gp120, HIV p24, NF-κB, E2F transcription factor, plasminogen activator inhibitor, Tenascin C, CXCL12/SDF-1, and prostate specific membrane antigen (PSMA).

The analyte may be a cell, such as, for example, gastric cancer cells (e.g., HGC-27 cells); non-small cell lung cancer (NSCLC) cells, colorectal cancer cells (e.g., DLD-1 cells), H23 lung adenocarcinoma cells, Ramos cells, T-cell acute lymphoblastic leukemia (T-ALL) cells, CCRF-CEM cells, acute myeloid leukemia (AML) cells (e.g., HL60 cells), small-cell lung cancer (SCLC) cells (e.g., NCI-H69 cells), human glioblastoma cells (e.g., U118-MG cells), prostate cancer cells (e.g., PC-3 cells), HER-2-overexpressing human breast cancer cells (e.g., SK-BR-3 cells), pancreatic cancer cells (e.g., Mia-PaCa-2)). In other embodiments, the analyte may be an infectious agent, such as a bacterium (e.g., *Mycobacterium tuberculosis, Staphylococcus aureus, Shigella dysenteriae, Escherichia coli* O157:H7, *Campylobacter jejuni, Listeria monocytogenes, Pseudomonas aeruginosa, Salmonella* O8, and *Salmonella enteritidis*), virus (e.g., retroviruses (such as HIV), herpesviruses, adenoviruses, lentiviruses, Filoviruses (e.g., West Nile, Ebola, and Zika viruses), hepatitis viruses (e.g., A, B, C, D, and E); HPV, Parvovirus, etc.), a parasite, or fungal spores.

Binding Surface

In some embodiments, the disclosed method comprises capturing an analyte of interest on one or more binding surfaces. In other embodiments, the disclosure provides a method comprises capturing first and second analytes (and optionally, third, fourth, fifth, and subsequent analytes) of interest on the surface of a first and second (and optionally, third, fourth, fifth, and subsequent) microparticles. In one embodiment, the first microparticle (i) comprises a plurality of specific binding members immobilized on the surface thereof which bind to the first analyte and (ii) is labeled with a first fluorophore, and the second microparticle comprises a plurality of specific binding members immobilized on the surface thereof which bind to the second analyte. In another embodiment, the first microparticle and the second microparticle differ in size and/or shape (e.g., round and oval microparticles).

In some embodiments, the microparticle may be between about 0.1 nm and about 10 microns, between about 50 nm and about 5 microns, between about 100 nm and about 1 micron, between about 0.1 nm and about 700 nm, between about 500 nm and about 10 microns, between about 500 nm and about 5 microns, between about 500 nm and about 3 microns, between about 100 nm and 700 nm, or between about 500 nm and 700 nm. For example, the microparticle may be about 4-6 microns, about 2-3 microns, about 0.5-1.5 microns, or about 1 micron. Particles less than about 500 nm are sometimes considered nanoparticles. Thus, the microparticle optionally may be a nanoparticle between about 0.1 nm and about 500 nm, between about 10 nm and about 500 nm, between about 50 nm and about 500 nm, between about 100 nm and about 500 nm, about 100 nm, about 150 nm, about 200 nm, about 250 nm, about 300 nm, about 350 nm, about 400 nm, about 450 nm, or about 500 nm.

In some embodiments, the binding surface (e.g., microparticles) may be ferromagnetic, ferrimagnetic, paramagnetic, superparamagnetic or ferrofluidic. Exemplary ferromagnetic materials include Fe, Co, Ni, Gd, Dy, CrO2, MnAs, MnBi, EuO, NiO/Fe. Examples of ferrimagnetic materials include NiFe2O4, CoFe2O4, Fe3O4 (or FeO·Fe2O3). The binding surface can have a solid core portion that is magnetic and is surrounded by one or more non-magnetic layers. Alternatively, the magnetic portion can be a layer around a non-magnetic core. Magnetic binding surfaces, such as microparticles, may be stored in dry form or in a liquid. A magnetic binding surface may be subjected to a magnetic field prior to or after contacting with the sample containing an analyte.

In certain embodiments, a binding surface (e.g., a microparticle) may also comprise a protective, blocking, or passivating layer that can eliminate or minimize non-specific attachment of non-capture components (e.g., analyte molecules, binding members) to the binding surface during the assay which may lead to false positive signals during detection or loss of signal. Examples of materials that may be utilized in certain embodiments to form passivating layers include, but are not limited to, polymers, such as poly(ethylene glycol), that repel the non-specific binding of proteins; naturally occurring proteins with this property, such as serum albumin and casein; surfactants, e.g., zwitterionic surfactants, such as sulfobetaines; naturally occurring long-chain lipids; polymer brushes, and nucleic acids, such as salmon sperm DNA.

The binding surface (e.g., one or more microparticles) may be contacted with a volume of the sample using any suitable method known in the art. Contacting may be achieved in a variety of different ways, including combining the sample with a binding member, exposing a target analyte to a binding member by introducing the binding member in close proximity to the analyte, and the like. The contacting may be repeated as many times as necessary.

Whatever method is used, the binding surface (e.g., the first and second microparticles) may be contacted with a volume of sample under conditions whereby any analyte present in the sample binds to a specific binding member immobilized on the binding surface, such as the surface of microparticles. In one embodiment, contact between the binding surface and the sample volume is maintained (i.e., incubated) for a sufficient period of time to allow for the binding interaction between the specific binding member and analyte to occur. In one embodiment, the sample volume is incubated on the binding surface for at least 30 seconds and at most 10 minutes. For example, the sample may be incubated with the microparticles for about 1, 2, 3, 4, 5, 6, 7, 8, or 9 minutes. In one embodiment, the sample may be incubated with the binding surface for about 2 minutes. In addition, the incubating may be in a binding buffer that facilitates the specific binding interaction, such as, for example, albumin (e.g., BSA), non-ionic detergents (Tween-20, Triton X-100), and/or protease inhibitors (e.g., PMSF). The binding affinity and/or specificity of a specific binding member may be manipulated or altered in the assay by varying the binding buffer. In some embodiments, the binding affinity and/or specificity may be increased by varying the binding buffer. In some embodiments, the binding affinity and/or specificity may be decreased by varying the binding buffer. Other conditions for the binding interaction, such as, for example, temperature and salt concentration, may also be determined empirically or may be based on manufacturer's instructions. For example, the contacting may be carried out at room temperature (21° C.-28° C., e.g., 23° C.-25° C.), 37° C., or 4° C.

As discussed above, certain methods disclosed herein are suitable for detecting more than two different analytes. Thus, in some embodiments, the method may comprise capturing a third, fourth, or subsequent analyte of interest on a surface of a third, fourth, or subsequent microparticle, wherein (i) each of the third, fourth, and subsequent analytes is different from each other and from the first and second analytes, and (ii) the third, fourth, or subsequent microparticle comprises a plurality of specific binding members immobilized on the surface thereof which bind to the third, fourth, or subsequent analyte. The method may further comprise reacting the captured third, fourth, or subsequent analyte with a third, fourth, or subsequent conjugate, wherein the third, fourth, or subsequent conjugate comprises a specific binding member that is labeled with a fourth, fifth, or subsequent fluorophore and binds to the third, fourth, or subsequent analyte, and wherein the fourth, fifth, and subsequent fluorophores are different from each other and from each of the first, second, and third fluorophores.

Specific Binding Members

As discussed above, the binding surface (e.g., a first microparticle) may have a plurality (e.g., 2 or more, 50 or more, 100 or more, 1,000 or more, or 5,000 or more) of specific binding members, each of which specifically binds to the analyte, immobilized on the surface of thereof.

It will be appreciated that the choice of specific binding members (e.g., first, second, third, fourth, or subsequent binding members) will depend on the analyte or analytes to be analyzed. Binding members for a wide variety of target molecules are known or can be readily found or developed using known techniques. For example, when the target analyte is a protein, the binding members may include peptides, proteins, particularly antibodies or fragments thereof (e.g., antigen-binding fragments (Fabs), Fab' fragments, and F(ab')$_2$ fragments), full-length monoclonal or polyclonal antibodies, antibody-like fragments, recombinant antibodies, chimeric antibodies, single-chain Fvs ("scFv"), single chain antibodies, single domain antibodies, such as variable heavy chain domains ("VHH"; also known as "VHH fragments") derived from animals in the Camelidae family (see, e.g., Gottlin et al., *Journal of Biomolecular Screening*, 14:77-85 (2009)), recombinant VHH single-domain antibodies, $V_{NAR}$ fragments, disulfide-linked Fvs ("sdFv"), anti-idiotypic ("anti-Id") antibodies, and functionally active epitope-binding fragments of any of the foregoing. The binding members also can be other proteins, such as receptor proteins, Protein A, Protein C, or the like. When the analyte is a small molecule, such as a steroid, bilin, retinoid, or lipid, the first and/or the second specific binding member may be a scaffold protein (e.g., lipocalins) or a receptor. In some embodiments, a specific binding member for protein analytes can be a peptide. In another embodiment, when the target analyte is an enzyme, suitable binding members may include enzyme substrates and/or enzyme inhibitors, such as a peptide, a small molecule, and the like. In some cases, when the target analyte is a phosphorylated species, the binding member may comprise a phosphate-binding agent. For example, the phosphate-binding agent may comprise metal-ion affinity media such as those described in U.S. Pat. No. 7,070,921 and U.S. Patent Application Publication 2006/0121544.

When the analyte is a carbohydrate, potentially suitable specific binding members (as defined herein) include, for example, antibodies, lectins, and selectins. As will be appreciated by those of ordinary skill in the art, any molecule that can specifically associate with a target analyte of interest may potentially be used as a binding member.

In certain embodiments, suitable target analyte/binding member complexes can include, but are not limited to, antibodies/antigens, antigens/antibodies, receptors/ligands, ligands/receptors, proteins/nucleic acid, enzymes/substrates and/or inhibitors, carbohydrates (including glycoproteins and glycolipids)/lectins and/or selectins, proteins/proteins, proteins/small molecules, etc.

Certain embodiments utilize binding members that are proteins or polypeptides. As is known in the art, any number of techniques may be used to attach a polypeptide to a solid surface or support, such as a microparticle. A wide variety of techniques are known for adding reactive moieties to proteins, such as, for example, the method described in U.S. Pat. No. 5,620,850. Methods for attachment of proteins to surfaces also are described in, for example, Heller, *Acc. Chem. Res.*, 23: 128 (1990).

As described herein, binding between the specific binding member(s) and the analyte is specific, e.g., as when the binding member and the analyte are complementary parts of a binding pair. For example, in one embodiment, the binding member may be an antibody that binds specifically to an epitope on an analyte. The antibody, according to one embodiment, can be any antibody capable of binding specifically to an analyte of interest. For example, appropriate antibodies include, but are not limited to, monoclonal antibodies, bispecific antibodies, minibodies, domain antibodies (dAbs) (e.g., such as described in Holt et al., *Trends in Biotechnology*, 21: 484-490 (2014)), single domain antibodies (sdAbs) that are naturally occurring, e.g., as in cartilaginous fishes and camelid, or which are synthetic, e.g., nanobodies, VHH, or other domain structure), synthetic antibodies (sometimes referred to as antibody mimetics), chimeric antibodies, humanized antibodies, antibody fusions (sometimes referred to as "antibody conjugates"), and fragments thereof. In another embodiment, the analyte molecule may be an antibody and the binding member may be a peptide that binds specifically to the antibody.

In some embodiments, the specific binding member may be a chemically programmed antibody (cpAb) (Rader, *Trends in Biotechnology*, 32:186-197 (2014)), bispecific cpAbs, antibody-recruiting molecules (ARMs) (McEnaney et al., *ACS Chem. Biol.*, 7: 1139-1151 (2012)), branched capture agents, such as a triligand capture agent (Millward et al., *J. Am. Chem. Soc.*, 133: 18280-18288 (2011)), engineered binding proteins derived from non-antibody scaffolds, such as monobodies (derived from the tenth fibronectin type III domain of human fibronectin), affibodies (derived from the immunoglobulin binding protein A), DARPins (based on Ankyrin repeat modules), anticalins (derived from the lipocalins bilin-binding protein and human lipocalin 2), and cysteine knot peptides (knottins) (Gilbreth and Koide, *Current Opinion in Structural Biology*, 22:1-8 (2012); Banta et al., *Annu. Rev. Biomed. Eng.*, 15: 93-113 (2013)), WW domains (Patel et al., *Protein Engineering, Design & Selection*, 26(4): 307-314 (2013)), repurposed receptor ligands, affitins (Béhar et al., *Protein Engineering, Design & Selection*, 26: 267-275 (2013)), and/or Adhirons (Tiede et al., *Protein Engineering, Design & Selection*, 27: 145-155 (2014)).

In embodiments where the analyte is a cell (e.g., mammalian, avian, reptilian, other vertebrate, insect, yeast, bacterial, cell, etc.), the specific binding member may be a ligand having specific affinity for a cell surface antigen (e.g., a cell surface receptor). In one embodiment, the specific binding member may be an adhesion molecule receptor or portion thereof, which has binding specificity for a cell adhesion molecule expressed on the surface of a target cell type. The adhesion molecule receptor binds with an adhesion molecule on the extracellular surface of the target cell, thereby immobilizing or capturing the cell. The bound cell may then be detected by using a second binding member that may be the same as the first binding member or may bind to a different molecule expressed on the surface of the cell.

In some embodiments, the binding affinity between analyte molecules and specific binding members should be sufficient to remain bound under the conditions of the assay, including wash steps to remove molecules or particles that are non-specifically bound. In some embodiments, for example, in the detection of certain biomolecules, the binding constant of the analyte molecule to its complementary binding member may be between at least about $10^4$ and about $10^6$ $M^{-1}$, at least about $10^5$ and about $10^9$ $M^{-1}$, at least about $10^7$ and about $10^9$ $M^{-1}$, greater than about $10^9$ $M^{-1}$.

A specific binding member may be attached to a binding surface (e.g., a microparticle) using any suitable method, a variety of which are known in the art. For example, a specific binding member may be attached to a binding surface via a linkage, which may comprise any moiety, functionalization, or modification of the microparticle and/or binding member that facilitates the attachment of the binding member to the microparticle. The linkage between the binding member and the binding surface may include one or more chemical or physical bonds and/or chemical spacers providing such bond(s) (e.g., non-specific attachment via van der Waals forces, hydrogen bonding, electrostatic interactions, hydrophobic/hydrophilic interactions; etc.). Any number of techniques may be used to attach a polypeptide to a wide variety of solid supports, such as those described in, for example U.S. Pat. No. 5,620,850, and Heller, *Acc. Chem. Res.*, 23: 128 (1990).

Following a sufficient incubation time between the binding surface (e.g., first and second microparticles) and the sample, an analyte of interest present in the sample desirably is captured on the binding surface via the specific binding members immobilized on the microparticle surface.

Macroconjugates

After an analyte of interest is captured on the binding surface, such as a plurality of microparticles, the method disclosed herein may comprise reacting a plurality (e.g., 2 or more, 50 or more, 100 or more, 1,000 or more, or 5,000 or more) of macroconjugates with the captured analyte. In one embodiment, each of the macroconjugates comprises: (i) a core which comprises a cross-linked protein or polymer comprising a polysaccharide, a dendrimer, a polyether compound, or nanoparticle; (ii) a plurality of specific binding members (e.g., antibodies), fragments thereof, or combinations thereof; (iii) a plurality of tags or detectable labels, and optionally (iv) a plurality of carrier proteins. When the macroconjugate comprises a plurality of tags, the methods described herein comprise reacting a plurality of fluorescent agents with the tags, wherein each fluorescent agent comprises a molecule which is capable of binding to the tag and a detectable label.

In other embodiments, each of the macroconjugates comprises (i) a core which comprises a cross-linked protein or polymer comprising a polysaccharide, a dendrimer, a polyether compound, or nanoparticle; (ii) a plurality of carrier proteins covalently attached to locations around the core (e.g., randomly); (iii) a plurality of specific binding members (e.g., antibodies), fragments thereof, or combinations thereof covalently attached to the carrier proteins; and (iv) a plurality of tags covalently attached to the plurality of carrier proteins or the plurality of antibodies. One or more fluorescent agents may be reacted with the macroconjugates, such that the fluorescent agents covalently bind to the macroconjugate core directly or via the aforementioned tags.

It will be appreciated that a "cross-linked" protein or polymer is formed when one protein or polymer chain is linked to another protein or polymer chain, such as by covalent or ionic linkages. A cross-linked polymer may comprise synthetic polymer chains or natural polymer chains (e.g., proteins or polysaccharides). The polysaccharide may be any suitable polymeric carbohydrate molecule composed of long chains of monosaccharide units bound together by glycosidic linkages. Suitable polysaccharides include, but are not limited to, cellulose, starches, glycogen, glucans, alginate, curdlan, dextran, gellan, hyalouran, levan, xanthan, and pullulan. In one embodiment, the polysaccharide is a dextran, amino dextran, or combinations thereof. The term "dendrimer," as used herein, refers to nano-sized, radially symmetric molecules with well-defined, homogeneous, and monodisperse structure consisting of tree-like arms or branches (Abassi et al., *Nanoscale Res Lett.*, 9(1): 247 (2014)). A variety of different dendrimers are known in the art and display biological properties such as polyvalency, self-assembling, electrostatic interactions, chemical stability, low cytotoxicity, and solubility. Examples of suitable dendrimers that can be used in the disclosed methods include, but are not limited to, a DNA dendrimer (see, e.g., Fu et al., *J Gene Med.*, 9(12): 1334-1342 (2008); and Fu et al., *J Gene Med.*, 9(3): 181-188 (2007)), and a polyamidoamine (PAMAM) dendrimer (Esfand et al., *Drug Discovery Today*, 6(8): 427-436 (2001)). The term "polyether," as used herein, refers to any of a group of polymers in which the repeating unit contains a carbon-oxygen bond derived especially from an aldehyde or an epoxide. In one embodiment, the polyether may be polyethylene glycol (PEG). The term "nanoparticle," as used herein, refers to an inorganic particle between 1 and 100 nanometres (nm) in size that functions as a whole unit with respect to its transport and properties. Whatever polymer or protein is used, it will be appreciated that the cross-linked polymer or protein functions as a scaffold onto which other elements of the complex described herein are attached.

The macroconjugates may further comprise a plurality (e.g., 2 or more, 50 or more, 100 or more, 1,000 or more, or 5,000 or more) of carrier proteins covalently attached to locations around the core (e.g., randomly). The term "carrier protein," as used herein, refers to a protein that improves the solubility, stability, reactivity, and/or specificity of the macroconjugate. Any suitable protein that can be covalently attached to the core may be used as the carrier protein. In one embodiment, the carrier proteins are serum albumin proteins. Serum albumin proteins are globular proteins produced by the liver and are the most abundant blood protein in mammals. The serum albumin proteins may be human serum albumin or bovine serum albumin. In other embodiments, the carrier proteins may be antigens or antibodies. Attachment of the carrier proteins around the core may be "random" in that it occurs without specificity or pattern. The covalent attachment of the plurality of carrier proteins to the core may be achieved by any suitable method known in the art, such as those described in, e.g., Mattson et al., *Molecular Biology Reports*, 17: 167-183 (1993); and Hermanson, G. T. (ed.), *Bioconjugate Techniques, 3rd Edition*, Academic Press (2013)).

The macroconjugates may also comprise a plurality (e.g., 2 or more, 50 or more, 100 or more, 1,000 or more, or 5,000 or more) of specific binding members (e.g., antibodies, fragments thereof, or combinations thereof covalently attached to the carrier proteins. The plurality of specific binding members or fragments thereof (e.g., antibodies or antibody fragments) specifically bind to the analyte, which results in the conjugation of the macroconjugate to the captured analyte and formation of an immunosandwich (also referred to herein as an "immunosandwich complex"). The specific binding member and/or fragment thereof may be a whole antibody or any suitable antibody fragment, such as those described above and known in the art. In one embodiment, the labeled immunosandwich complex comprises an antibody fragment, such as an antigen-binding fragment (Fab).

The macroconjugates may further comprise a plurality (e.g., 2 or more, 50 or more, 100 or more, 1,000 or more, or 5,000 or more) of tags covalently attached to the macroconjugate core, the plurality of carrier proteins, and/or to the plurality of specific binding members. The term "tag," as used herein, refers to a molecule or compound that can bind (i.e., attach) a fluorescent agent to the macroconjugate. The tag may be a polymer (e.g., an anionic or cationic polymer), a protein (e.g., a globular protein) which does not interfere with the assay, a polynucleotide (e.g, DNA or RNA), or a nanoparticle. In some embodiments, the tag may be an affinity tag. The term "affinity tag," as used herein, is a type of epitope tag that is recombinantly fused to the N- or C-terminus of a protein which typically facilitates affinity purification of the protein. Affinity tags generally are small in size and inert so as to limit any potential interaction with the protein or other proteins that may be present in culture media. Examples of affinity tags include, but are not limited to, biotin, glutathione-S-transferase (GST), a poly(His) tag, chitin binding protein (CBP), maltose binding protein (MBP), and a FLAG tag. In one embodiment, the tag comprises biotin. In another embodiment, the tag comprises a molecule or compound that binds to the fluorescent agent. For example, the tag may comprise an antibody that specifically binds to a fluorophore or an aptamer (e.g., an anti-fluorescein antibody). The term "aptamer," as used herein, refers to an oligonucleotide or peptide molecule that can bind to pre-selected targets including small molecules, proteins, and peptides among others with high affinity and specificity. Antibodies which bind to fluorophores and/or aptamers are known in the art and commercially available from a variety of sources (e.g., ThermoFisher Scientific and Bio-Rad Laboratories, Inc.). The plurality of tags may be covalently attached to the macroconjugate core, the plurality of carrier proteins, and/or the plurality of antibodies using cross-linking methodology described herein and known in the art, or through the use of cleavable linker molecules, such as those described in, e.g., International Patent Application Publication WO 2017/004463A1.

An exemplary macroconjugate is schematically depicted in FIG. 1. Immunosandwich formation may be carried out under conditions sufficient for a binding interaction between the analyte and antibody or antibody fragment. Following reaction of the analytes with the antibody or antibody fragments (e.g., via the macroconjugates), any antibody, antibody fragment, or component of the macroconjugate not bound to the analyte may be removed, followed by an optional wash step. Any unbound antibody, antibody fragment, or component of the macroconjugates may be separated from the immunosandwich by any suitable means such as, for example, droplet actuation, electrophoresis, electrowetting, dielectrophoresis, electrostatic actuation, electric field mediated, electrode mediated, capillary force, chromatography, centrifugation, aspiration, or surface acoustic wave (SAW)-based washing methods.

When the method comprises analyzing two or more analytes of interest in a biological sample in a single assay, after the first and second analytes of interest are captured on the surface of the first and second microparticles, respectively, the method comprises reacting the captured first analyte of interest with a first conjugate and reacting the second analyte of interest with a second conjugate, wherein the first conjugate comprises a specific binding member that is labeled with a second fluorophore and binds to the first analyte and the second conjugate comprises a specific binding member that is labeled with a third fluorophore and binds to the second analyte. The term "conjugate," as used herein, refers to a complex comprising a specific binding pair member and a detectable label. The specific binding pair member may be an antibody or antibody fragment as discussed herein. Thus, the binding pair member of the conjugate specifically binds to the analyte, which results in the linkage of the conjugate to the captured analyte and formation of an immunosandwich.

Fluorescent Agents

In some embodiments, the macroconjugates comprise a plurality of fluorescent agents covalently attached to the macroconjugate core or the plurality of specific binding members. In other embodiments, the methods described herein comprise reacting a plurality of fluorescent agents with the macroconjugates. Each fluorescent agent comprises (1) a molecule which is capable of binding to the macroconjugate core or a tag and (2) a detectable label. In some embodiments, multiple fluorescent agents may simultaneously bind to a single macroconjugate, allowing for the direct detection of a single immunosandwich on a microparticle. The choice of molecule used in the fluorescent agent will depend on the tag that is used in the macroconjugate. In certain embodiments, the molecule is a protein. In embodiments where the tag is biotin, streptavidin may be the protein in the fluorescent agent which is capable of binding to the macroconjugate core or the tag. In embodiments where the tag is an antibody, then the molecule in the fluorescent agent may be a fluorophore, an aptamer, or an antigen that specifically binds to the antibody.

In some embodiments, the first microparticle as described above comprises a first fluorophore, while the specific binding members of the first and second conjugates are labeled with a second and third fluorophore, respectively. In this embodiment, the first, second, and third fluorophores are different. Following reaction of the first and second captured analytes with the first and second conjugates, any specific binding member (e.g., antibody or antibody fragment), or component of the conjugate not bound to the captured analyte may be removed, followed by an optional wash step. Any unbound antibody, antibody fragment, or component of the conjugates may be separated from the immunosandwich by any suitable means such as, for example, droplet actuation, electrophoresis, electrowetting, dielectrophoresis, electrostatic actuation, electric field mediated, electrode mediated, capillary force, chromatography, centrifugation, aspiration, or surface acoustic wave (SAW)-based washing methods.

Any suitable fluorescent compound known in the art can be used as a detectable label. Examples of suitable fluorescent compounds include, but are not limited to, 5-fluorescein, 6-carboxyfluorescein, 3'6-carboxyfluorescein, 5(6)-carboxyfluorescein, 6-hexachloro-fluorescein, 6-tetrachlorofluorescein, fluorescein isothiocyanate, rhodamine, phycobiliproteins, phycoerythrin, R-phycoerythrin, and allophycocyanin), quantum dots (e.g., zinc sulfide-capped cadmium selenide), a thermometric label, or an immuno-polymerase chain reaction label. In particular, phycoerythrin (PE) an allophycocyanin (APC) are examples of highly fluorescent compounds that may be included in the fluorescent agent. R-Phycoerythrin, or PE, is used in the art as a fluorescence-based indicator for labeling antibodies or other molecules in a variety of applications. R-Phycoerythrin absorbs strongly at about 566 nm with secondary peaks at 496 and 545 nm and emits strongly at 575 nm. R-Phycoerythrin is among the brightest fluorescent dyes ever identified. Similar to PE, APC is a highly fluorescent protein, but with emission at 680 nm. In one embodiment, the tag comprises biotin, and the plurality of fluorescent agents comprises streptavidin-phycoerythrin conjugates (SAPE) or streptavidin-allophycocyanin (SAAPC) conjugates. SAPE comprises the biotin-binding protein streptavidin covalently attached to a R-phycoerythrin, while SAAPC comprises streptavidin covalently attached to allophycocyanin. Both SAPE and SAAPC are commercially available from a variety of sources, such as, e.g., ThermoFisher Scientific (Waltham, MA) and ProZyme (Hayward, CA).

Detectable labels, labeling procedures, and detection of labels are described in Polak and Van Noorden, *Introduction to Immunocytochemistry*, 2nd ed., Springer Verlag, N.Y. (1997), and in Haugland, *Handbook of Fluorescent Probes and Research Chemicals* (1996), Molecular Probes, Inc., Eugene, Oregon.

It will be appreciated that different conformations of the analyte capture and immunosandwich formation methods described above are within the scope of the present disclosure. Indeed, the various components of the macroconjugates and the fluorescent agents described above may be arranged or utilized in any suitable combination, conformation, or format.

The presence or amount of analyte of interest present in a sample can be determined (e.g., quantified) using any suitable method known in the art. Such methods include, but are not limited to, immunoassays. Any suitable immunoassay may be utilized, such as, for example, a sandwich immunoassay (e.g., monoclonal-polyclonal sandwich immunoassays, competitive inhibition immunoassay (e.g., forward and reverse), a competitive binding assay, heterogeneous assay, and capture on the fly assay. In some embodiments, one tag is attached to a capture antibody and a detection antibody. Immunoassay components and techniques that may be used in the disclosed methods are further described in, e.g., International Patent Application Publication Nos. WO 2016/161402 and WO 2016/161400.

The disclosed method may comprise quality control components. "Quality control components" in the context of immunoassays and kits described herein, include, but are not limited to, calibrators, controls, and sensitivity panels. A "calibrator" or "standard" can be used (e.g., one or more, such as a plurality) in order to establish calibration (standard) curves for interpolation of the concentration of an analyte, such as an antibody. Alternatively, a single calibrator, which is near a reference level or control level (e.g., "low", "medium", or "high" levels), can be used. Multiple calibrators (i.e., more than one calibrator or a varying amount of calibrator(s)) can be used in conjunction to comprise a "sensitivity panel." The calibrator is optionally, and is preferably, part of a series of calibrators in which each of the calibrators differs from the other calibrators in the series, such as, for example, by concentration or detection method (e.g., colorimetric or fluorescent detection).

Multiplexing

The disclosed methods may include two or more (e.g., 2, 3, 4, 5, or more) microparticles and specific binding members to detect two or more (e.g., 2, 3, 4, 5, or more) target analytes in a sample, which is referred to herein as a "multiplex immunoassay" or "multiplex assay." Each of the specific binding members binds to a different analyte, and each specific binding member and/or microparticle may comprise a different detectable label. Indeed, in one embodiment, the disclosure provides a method comprising (a) capturing a first analyte of interest on a surface of a first microparticle, wherein the first microparticle (i) comprises a plurality of specific binding members immobilized on the surface thereof which bind to the first analyte and (ii) is labeled with a first fluorophore; (b) capturing a second analyte of interest on a surface of a second microparticle, wherein (i) the first analyte is different from the second analyte, and (ii) the second microparticle comprises a plurality of specific binding members immobilized on the surface thereof which bind to the second analyte. In another embodiment, the method comprises (a) capturing a first analyte of interest on a surface of a first microparticle, wherein the first microparticle comprises a plurality of specific binding members immobilized on the surface thereof which bind to the first analyte; (b) capturing a second analyte of interest on a surface of a second microparticle, wherein (i) the first analyte is different from the second analyte, (ii) the second microparticle comprises a plurality of specific binding members immobilized on the surface thereof which bind to the second analyte, and (iii) the first microparticle and the second microparticles differ in size and/or shape.

Imaging and Analysis

Immunoassays traditionally have been performed using fluorescence, chemiluminescence, or other means of generating a signal in response to an analyte. Many immunoassays are performed by measuring the intensity of a light signal generated in the total volume of a reaction mixture. The light signal generated can be measured by an optical means, wherein the light signal generated is emitted by a large number of molecules. Typically, as described herein, immunoassays may involve combining a sample suspected of containing an antigen with a reagent comprising a first antibody bound to a solid support, e.g., a planar surface (e.g., flat plate or biochip), a bead, or a microparticle, to form a reaction mixture. The antigen, if present in the sample, specifically binds to the first antibody. A conjugate, which comprises a second antibody having a label attached thereto, is introduced to the reaction mixture and specifically binds to the antigen, which is specifically bound to the first antibody, which, as stated previously, is bound to the solid support. The signal attributable to the label is then measured after unbound conjugate is removed from the reaction mixture, typically by performing a wash step. The signal that is derived from the total volume of the reaction mixture is measured and then compared to a calibration curve to establish the concentration of antigen present in the sample.

Light intensity may be measured using light emitting diodes (LEDs) and/or lasers and detectors, which can provide qualitative assessments of sample properties such as color, volume, and sample layer separation. Two-dimensional detection systems such as, for example, charged-coupled device (CCD) cameras, also are used for detecting fluorescence or chemiluminescent light of a sample. Commercially available systems have either an optical imaging system which projects the binding surface provided with chemiluminescent markers or fluorescent markers on a CCD sensor by using lens optics, or a combination of image intensifier and CCD camera. For spatially resolved, fluorescence-optical detection of substances immobilized on a planar surface (e.g., a biochip), "scanners" may be used which scan the surface of the chip using a focused laser beam, allowing for detection of the emitted fluorescence light. Exemplary fluorescence scanners are described in, e.g., U.S. Pat. Nos. 5,837,475 and 5,945,679. Scanners in which a confocal excitation and detection system has been integrated into an epifluorescence microscope are also known. The systems used in scanners for detecting the emitted fluorescence light are usually "one-channel systems", i.e., for example, individual photocells or secondary electron multipliers (photomultipliers).

In the methods described herein, spatial information and/or information related to individual immunosandwich complexes comprising an analyte from the sample improve the sensitivity of the assay over conventional methods. By incorporating spatial information that is not contained in conventional ligand-receptor binding assays, aggregation of reagents and non-specific binding, for example, can be eliminated from the signal generated and the analyte in the sample can be qualified and simultaneously or subsequently quantified. For example, with respect to qualification, undesired background signal associated with a solid phase, such as, for example, microparticles, can be examined and removed before the use of intensity information.

In this regard, the methods described herein further comprises imaging the binding surface(s) (e.g., one or more microparticles) on which immunosandwiches have been formed, as described above, and analyzing the resulting images. In some embodiments, the immunosandwich-containing surfaces are imaged on any solid support (e.g., any planar (flat) surface, such as, for example, a microfluidic channel on a detection slide). Imaging systems suitable for use in the method described herein can be any system capable of acquiring images such that individual binding surfaces (e.g., microparticles) and/or information related to individual immunosandwich complexes can be resolved. Imaging devices suitable for use with the method described herein include, but are not limited to, light microscopes, scanning microscopes, fluorescence imaging scanners, and the like.

In one embodiment using the principles of the present invention, one or more fluorescent images of one or more binding surfaces is captured and intensity of the fluorescent image is calculated.

In another embodiment, imaging the binding surface(s), such as the surface of microparticles, involves acquiring a transmitted light image of the microparticles and one or more fluorescent images corresponding to the fluorescent agents. The transmitted light image may be employed to locate all image areas containing binding surfaces, e.g., microparticle surfaces. A fluorescence image is then acquired to determine the location and/or intensity of fluorescent agents directly bound to the binding surface(s). The fluorescence image uses a color (e.g., red, green, blue), which, in some embodiments, corresponds to a first, second, and third fluorophore. The resulting transmitted light and fluorescent images may then be analyzed using any suitable method, which, in some embodiments, includes the generation of image masks (see, FIG. 2).

The mask generally defines regions of interest and areas to be disregarded when performing the analysis. In one embodiment shown in FIG. 2, all image areas containing a binding surface are defined as a region of interest to be analyzed (i.e., the light colored portions (see dotted white arrow in FIG. 2)) and the remaining area is disregarded (i.e., the dark color portions (see solid white arrow in FIG. 2)). For the region of interest, a region of interest area is calculated. The mask is then applied to the one or more fluorescent images to determine the total fluorescent intensity from the region of interest. In one embodiment, the total fluorescent intensity may be measured as total "counts" of intensity, and the region of interest may be measured in pixels. Thus, counts per pixel ("CPP") can be calculated in an analog mode. In some embodiments, the one or more acquired fluorescent images may be analyzed in digital mode and/or analog mode. If the signal value calculated in analog mode, such as the CPP, is below a predetermined value, then image analysis may be switched from analog to digital mode. Other methods for determining analog and/or digital mode as known in the art can also be used. As described above, digital mode involves using the region of interest and counting the total number of high intensity peaks on the binding surface(s). The ratio of total number of high intensity peaks to region of interest area may then be determined and expressed as "peaks per area" or "PPA." Each high intensity peak identified on the binding surface corresponds to a single immunosandwich complex. A high intensity peak may be a single pixel or a cluster of pixels which intensities are above a predetermined threshold. The predetermined threshold (also referred to herein as "preset value") chosen will depend upon, inter alia, the analyte of interest and the detectable label used. This analysis is illustrated schematically in FIG. 2 and also described in Example 2 (where the preset value used was 1000; however, in alternative embodiments, the preset value could be less than 1000 or greater than 1000). In some embodiments, if the average pixel intensity in the region of interest is less than a predetermined value, analyzing the images comprises: (i) counting high fluorescence intensity peaks in the region of interest; (ii) determining the ratio of peaks to the region of interest area in the one or more fluorescent images; and (iii) calculating the composite signal using a conversion factor to combine the data points obtained for different analyte concentrations.

Figure 9:
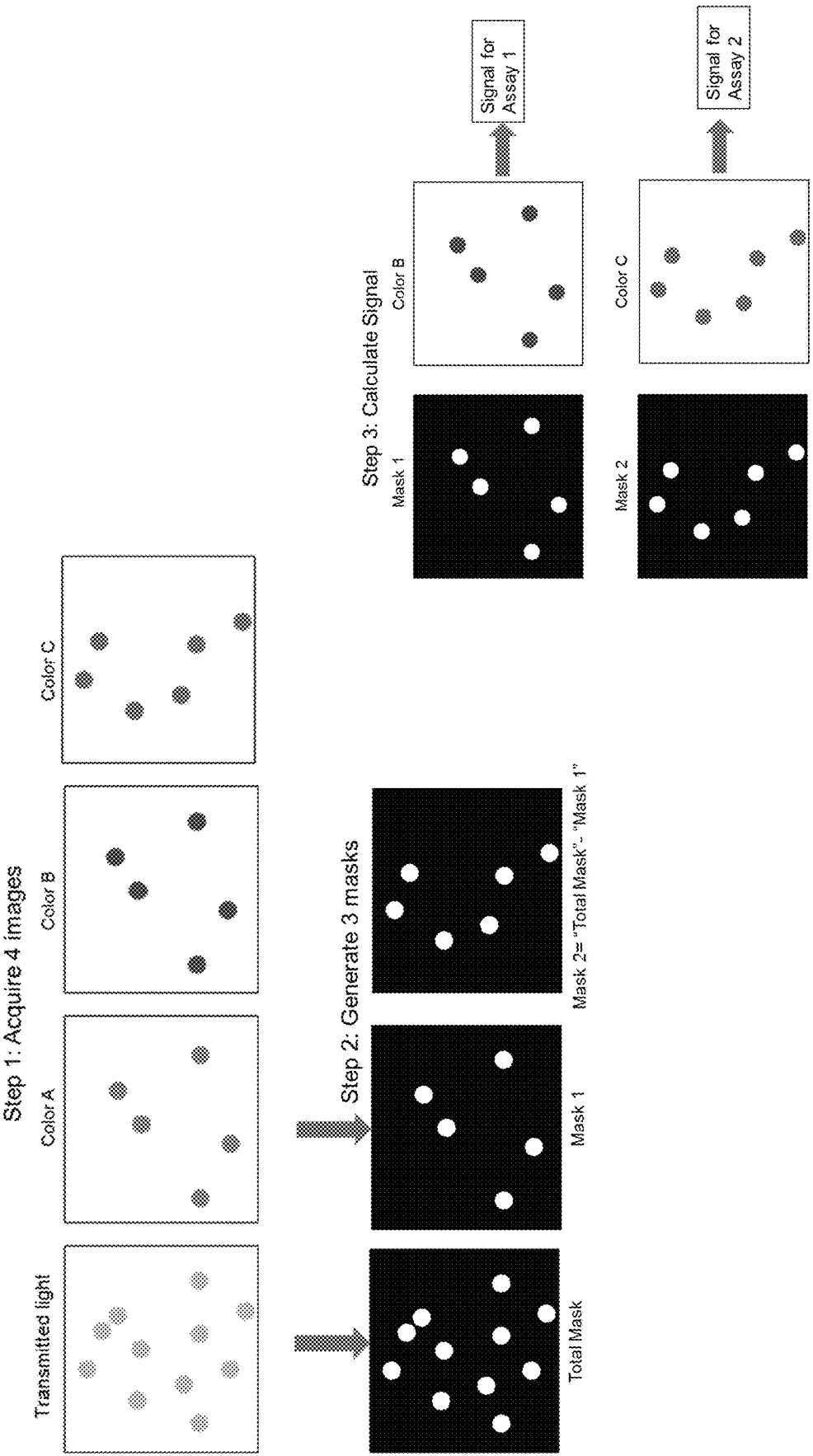
FIG. 9 is a diagram illustrating the analysis of a duplex immunosandwich assay according to the present disclosure. The assay comprises reagents for analyte 1 (i.e., microparticle 1 "MP1" and Conjugate 1) and analyte 2 (MP2 and Conjugate 2). MP1 is stained with a first fluorophore (color A). Conjugate 1 is labeled with a second fluorophore (color B), and Conjugate 2 is labeled with a third fluorophore (Color C).
Figure 10:
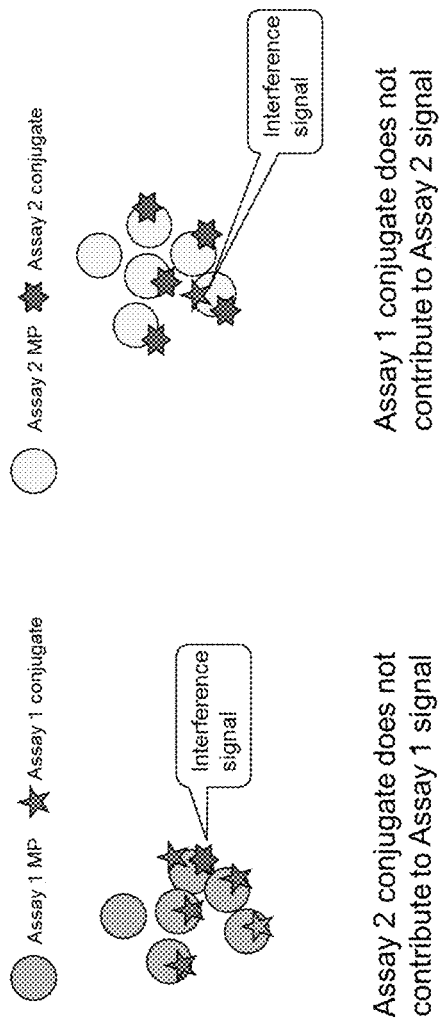
FIG. 10 is a diagram illustrating the reduced reagent interference provided by the assay methods described herein.

In multiplexing methods, images may be analyzed using a customized image analysis process that involves image subtraction. The image analysis process is "customized" in that it can be built or modified according to the particular analytes, sample, and assay conditions employed in the disclosed methods. In one embodiment, the customized image analysis process comprises generating a series of image "masks" using the transmitted light and fluorescent images acquired as described above. For example, the images are analyzed by (i) generating a total image mask based on the transmitted light image; (ii) generating a first image mask based on the fluorescent image corresponding to the first fluorophore; and (iii) subtracting the first image mask from the total image mask to generate a second image mask. For example, when one transmitted light image and three fluorescent images corresponding to the first, second, and third fluorophores, are acquired (for a total of four images), the total image mask is based on contrast and includes all microparticles employed in a single assay. A fluorescent image in the color of the first fluorophore may be used to generate the first image mask ("Mask 1") and includes only the first microparticles, with or without the first captured analyte. The second image mask ("Mask 2") may then be generated by subtracting the first image mask from the total image mask and includes only the second microparticles comprising the second captured analyte. Following generation of the image masks, the method further comprises calculating the signal emitted from the second fluorophore using the first image mask, whereby the first analyte is detected, and calculating the signal emitted from the third fluorophore using the second image mask, whereby the second analyte is detected. Generation and analysis of image masks in a multiplex immunoassay to detect first and second analytes of interest is illustrated schematically in FIG. 9 and FIG. 10. It will be appreciated that additional image masks may be generated and analyzed as described above depending on the total number of target analytes assessed by a particular multiplex immunoassay. In embodiments where no analytes of interest are present in a sample (e.g., a negative sample), the only detectable signal will be that of the first microparticle labeled with the first fluorophore, but in some embodiments non-specific binding may occur resulting in a detectable, albeit weak, signal.

The average value of intensity per pixel of the analyzed binding surface(s) may be measured in order to compare the intensity to a calibration curve that establishes concentration of the analyte as a function of intensity. The average value of intensity per pixel of the qualified microparticles can be determined using, for example, a CCD camera or a complementary metal-oxide semiconductor (CMOS) camera, which are capable of measuring intensity of light. The measurement of intensity may be converted to a parameter, which is designated in the units of counts. Each pixel has a number corresponding to the intensity of light measured at that pixel. The quantity of signal measured from the label of the fluorescent agents determines the concentration of the analyte.

In other embodiments, the methods described herein may be used in conjunction with methodologies for analyzing (e.g., detecting and/or quantifying) an analyte at the single molecule level. Any suitable technique for analyzing single molecules and single molecule interactions may be used in the context of the present disclosure, a variety of which are known in the art. Such single molecule (SM) detection techniques include, but are not limited to, single molecule fluorescence resonance energy transfer (FRET) (see, e.g., Keller et al., *J. Am. Chem. Soc.,* 136: 4534-4543 (2014); and Kobitski et al., *Nucleic Acids Res.,* 35: 2047-2059, (2007)), real-time single molecule coimmunoprecipitation (see, e.g., Lee et al., *Nat. Protoc.,* 8: 2045-2060 (2013)), single molecule electron transfer (see, e.g., Yang et al., *Science,* 302: 262-266 (2003); and Min et al., *Phys. Rev. Lett.,* 94: 198302 (2005)); single molecule force spectroscopy methods (see, e.g., Capitanio, M. & Pavone, F. S., *Biophys. J.,* 105: 1293-1303 (2013); and Lang et al., *Biophys. J.,* 83: 491-501 (2009)), cell extract pull-down assays (see, e.g., Jain et al., *Nature,* 473: 484-488, (2011); and Jain et al., *Nat. Protoc.,* 7: 445-452 (2012)), use of molecular motors (see, e.g., Yildiz et al., *Science,* 300(5628): 2061-2065 (2003)); and single molecule imaging in living cells (see, e.g., Sako et al., *Nat. Cell. Biol.,* 2(3): 168-172 (2000)), nanopore technology (see, e.g., International Patent Application Publication WO 2016/161402), nanowell technology (see, e.g., see, e.g., International Patent Application Publication WO 2016/161400), and single molecule total internal reflection fluorescence (TIRF) microscopy (see, e.g., Reck-Peterson et al., *Cold Spring Harb. Protoc.,* 2010(3):pdb.top73. doi: 10.1101/pdb.top73 (March 2010); and Kukalkar et al., *Cold Spring Harb. Protoc.,* 2016(5):pdb.top077800. doi: 10.1101/pdb.top077800 (May 2016)).

Variations on Methods

The disclosed methods of determining the presence or amount of two or more analytes of interest present in a sample may be as described herein. The methods may also be adapted in view of other methods for analyzing analytes. Examples of well-known variations include, but are not limited to, immunoassay, such as sandwich immunoassay (e.g., monoclonal-monoclonal sandwich immunoassays, monoclonal-polyclonal sandwich immunoassays, including enzyme detection (enzyme immunoassay (EIA) or enzyme-linked immunosorbent assay (ELISA), competitive inhibition immunoassay (e.g., forward and reverse), enzyme multiplied immunoassay technique (EMIT), a competitive binding assay, bioluminescence resonance energy transfer (BRET), one-step antibody detection assay, homogeneous assay, heterogeneous assay, capture on the fly assay, single molecule detection assay, etc. Such methods are disclosed in, for example, U.S. Pat. Nos. 6,143,576; 6,113,855; 6,019,944; 5,985,579; 5,947,124; 5,939,272; 5,922,615; 5,885,527; 5,851,776; 5,824,799; 5,679,526; 5,525,524; and 5,480,792; International Patent Application Publications WO 2016/161402 and WO 2016/161400; and Adamczyk et al., *Anal. Chim. Acta,* 579(1): 61-67 (2006).

Device for Analyte Analysis

The methods described herein can be performed using any device suitable for analyte analysis, a variety of which are known in the art and include, for example, peristaltic pump systems (e.g., FISHERBRAND™ Variable-Flow Peristaltic Pumps, ThermoFisher Scientific, Waltham, MA; and peristaltic pump systems available from MilliporeSigma, Burlington, MA), automated/robotic sample delivery systems (commercially available from e.g., Hamilton Robotics, Reno, NV; and ThermoFisher Scientific, Waltham, MA), microfluidics devices, droplet based microfluidic devices, digital microfluidics devices (DMF), surface acoustic wave based microfluidic (SAW) devices, or electrowetting on dielectric (EWOD) digital microfluidics devices (see, e.g., Peng et al., *Lab Chip,* 14(6): 1117-1122 (2014); and Huang et al., *PLoS ONE,* 10(5): e0124196 (2015)), and other automated systems such as Kingfisher™ instruments (ThermoFisher Scientific, Waltham, MA), ARCHITECT™ analyzers (Abbott, Abbott Park, IL), and other automated instruments known in the art.

In one embodiment, the methods described herein may be performed using a microfluidics device, such as a digital microfluidic (DMF) device. Any suitable microfluidics device known in the art can be used to perform the methods described herein. Exemplary microfluidic devices that may be used in the present methods include those described in, for example, International Patent Application Publication Nos. WO 2007/136386, WO 2009/111431, WO 2010/040227, WO 2011/137533, WO 2013/066441, WO 2014/062551, and WO 2014/066704, and U.S. Pat. No. 8,287,808. In certain cases, the device may be a lab-on-chip device, where analyte analysis may be carried out in a droplet of the sample containing or suspected of containing an analyte.

In one embodiment, at least two steps of the method described herein (e.g., 2, 3, or all steps) are carried out in a digital microfluidics device. The terms "digital microfluidics (DMF)," "digital microfluidic module (DMF module)," or "digital microfluidic device (DMF device)" are used interchangeably herein and refer to a module or device that utilizes digital or droplet-based microfluidic techniques to provide for manipulation of discrete and small volumes of liquids in the form of droplets. Digital microfluidics uses the principles of emulsion science to create fluid-fluid dispersion into channels (principally water-in-oil emulsion), and allows for the production of monodisperse drops/bubbles with a very low polydispersity. Digital microfluidics is based upon the micromanipulation of discontinuous fluid droplets within a reconfigurable network. Complex instructions can be programmed by combining the basic operations of droplet formation, translocation, splitting, and merging.

Digital microfluidics operates on discrete volumes of fluids that can be manipulated by binary electrical signals. By using discrete unit-volume droplets, a microfluidic operation may be defined as a set of repeated basic operations, i.e., moving one unit of fluid over one unit of distance. Droplets may be formed using surface tension properties of the liquid. Actuation of a droplet is based on the presence of electrostatic forces generated by electrodes placed beneath the bottom surface on which the droplet is located. Different types of electrostatic forces can be used to control the shape and motion of the droplets. One technique that can be used to create the foregoing electrostatic forces is based on dielectrophoresis which relies on the difference of electrical permittivities between the droplet and surrounding medium and may utilize high-frequency AC electric fields. Another technique that can be used to create the foregoing electrostatic forces is based on electrowetting, which relies on the dependence of surface tension between a liquid droplet present on a surface and the surface on the electric field applied to the surface.

In another embodiment, the methods described herein may be implemented in conjunction with a surface acoustic wave (SAW) based microfluidic device as a front-end assay processing method. The term "surface acoustic wave (SAW)," as used herein, refers generally to propagating acoustic waves in a direction along a surface. "Travelling surface acoustic waves" (TSAWs) enable coupling of surface acoustic waves into a liquid. In some embodiments, the coupling may be in the form of penetration or leaking of the surface acoustic waves into the liquid. In other embodiments, the surface acoustic waves are Rayleigh waves (see, e.g., Oliner, A. A. (ed), Acoustic Surface Waves. Springer (1978)). Propagation of surface acoustic waves may be conducted in a variety of different ways and by using different materials, including generating an electrical potential by a transducer, such as a series or plurality of electrodes, or by streaming the surface acoustic waves through a liquid.

In some embodiments, the DMF device or the SAW device is fabricated by roll to roll based printed electronics method. Examples of such devices are described in International Patent Application Publication Nos. 2016/161402 and WO 2016/161400.

Many of the devices described above allow for the detection of a single molecule of an analyte of interest. Other devices and systems known in the art that allow for single molecule detection of one or more analytes of interest also can be used in the methods described herein. Such devices and systems include, for example, Quanterix SIMOA™ (Lexington, MA) technology, Singulex's single molecule counting (SMC™) technology (Alameda, CA, see for example, U.S. Pat. No. 9,239,284), and devices described in, for example, U.S. Patent Application Publication Nos. 2017/0153248 and 2018/0017552.

Kits and Cartridges

Also provided herein is a kit for use in performing the above-described methods. The kit may be used with the disclosed device. Instructions included in the kit may be affixed to packaging material or may be included as a package insert. The instructions may be written or printed materials, but are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" may include the address of an internet site that provides the instructions.

The kit may include a cartridge that includes a microfluidics module. In some embodiments, the microfluidics module may be integrated in a cartridge. The cartridge may be disposable. The cartridge may include one or more reagents useful for practicing the methods disclosed above. The cartridge may include one or more containers holding the reagents, as one or more separate compositions, or, optionally, as admixture where the compatibility of the reagents will allow. The cartridge may also include other material(s) that may be desirable from a user standpoint, such as buffer(s), a diluent(s), a standard(s) (e.g., calibrators and controls), and/or any other material useful in sample processing, washing, or conducting any other step of the assay. The cartridge may include one or more specific binding members as described above.

The kit may further comprise reference standards for quantifying the analyte of interest. The reference standards may be employed to establish standard curves for interpolation and/or extrapolation of the analyte of interest concentrations. The kit may include reference standards that vary in terms of concentration level. For example, the kit may include one or more reference standards with either a high concentration level, a medium concentration level, or a low concentration level. In terms of ranges of concentrations for the reference standard, this can be optimized per the assay. Exemplary concentration ranges for the reference standards include but are not limited to, for example: about 10 fog/mL, about 20 fg/mL, about 50 fg/mL, about 75 fg/mL, about 100 fg/mL, about 150 fg/mL, about 200 fg/mL, about 250 fg/mL, about 500 fg/mL, about 750 fg/mL, about 1000 fg/mL, about 10 pg/mL, about 20 pg/mL, about 50 pg/mL, about 75 pg/mL, about 100 pg/mL, about 150 pg/mL, about 200 pg/mL, about 250 pg/mL, about 500 pg/mL, about 750 pg/mL, about 1 ng/mL, about 5 ng/mL, about 10 ng/mL, about 12.5 ng/mL, about 15 ng/mL, about 20 ng/mL, about 25 ng/mL, about 40 ng/mL, about 45 ng/mL, about 50 ng/mL, about 55 ng/mL, about 60 ng/mL, about 75 ng/mL, about 80 ng/mL, about 85 ng/mL, about 90 ng/mL, about 95 ng/mL, about 100 ng/mL, about 125 ng/mL, about 150 ng/mL, about 165 ng/mL, about 175 ng/mL, about 200 ng/mL, about 225 ng/mL, about 250 ng/mL, about 275 ng/mL, about 300 ng/mL, about 400 ng/mL, about 425 ng/mL, about 450 ng/mL, about 465 ng/mL, about 475 ng/mL, about 500 ng/mL, about 525 ng/mL, about 550 ng/mL, about 575 ng/mL, about 600 ng/mL, about 700 ng/mL, about 725 ng/mL, about 750 ng/mL, about 765 ng/mL, about 775 ng/mL, about 800 ng/mL, about 825 ng/mL, about 850 ng/mL, about 875 ng/mL, about 900 ng/mL, about 925 ng/mL, about 950 ng/mL, about 975 ng/mL, about 1000 ng/mL, about 2 µg/mL, about 3 µg/mL, about 4 µg/mL, about 5 µg/mL, about 6 µg/mL, about 7 µg/mL, about 8 µg/mL, about 9 µg/mL, about 10 µg/mL, about 20 µg/mL, about 30 µg/mL, about 40 µg/mL, about 50 µg/mL, about 60 µg/mL, about 70 µg/mL, about 80 µg/mL, about 90 µg/mL, about 100 µg/mL, about 200 µg/mL, about 300 µg/mL, about 400 µg/mL, about 500 µg/mL, about 600 µg/mL, about 700 µg/mL, about 800 µg/mL, about 900 µg/mL, about 1000 µg/mL, about 2000 µg/mL, about 3000 µg/mL, about 4000 µg/mL, about 5000 µg/mL, about 6000 µg/mL, about 7000 µg/mL, about 8000 µg/mL, about 9000 µg/mL, or about 10000 µg/mL.

The kit may include reagents for labeling the specific binding members, reagents for detecting the specific binding members and/or for labeling the analytes, and/or reagents for detecting the analyte. The kit may also include components to elicit cleavage of a tag, such as a cleavage mediated reagent. For example, a cleavage mediate reagent may include a reducing agent, such as dithiothreitol (DTT) or tris(2-carboxyethyl)phosphine) TCEP. The specific binding members, calibrators, and/or controls can be provided in separate containers or pre-dispensed into an appropriate assay format or cartridge.

The kit may also include quality control components (for example, sensitivity panels, calibrators, and positive controls). Preparation of quality control reagents is well-known in the art and is described on insert sheets for a variety of immunodiagnostic products. Sensitivity panel members optionally are used to establish assay performance characteristics, and are useful indicators of the integrity of the kit reagents and the standardization of assays.

The kit may also optionally include other reagents required to conduct a diagnostic assay or facilitate quality control evaluations, such as buffers, salts, enzymes, enzyme co-factors, substrates, detection reagents, and the like. Other components, such as buffers and solutions for the isolation and/or treatment of a test sample (e.g., pretreatment reagents), also can be included in the kit. The kit may additionally include one or more other controls. One or more of the components of the kit can be lyophilized, in which case the kit can further comprise reagents suitable for the reconstitution of the lyophilized components. One or more of the components may be in liquid form.

The various components of the kit optionally are provided in suitable containers as necessary. The kit further can include containers for holding or storing a sample (e.g., a container or cartridge for a urine, saliva, plasma, cerebrospinal fluid, or serum sample, or appropriate container for storing, transporting or processing tissue so as to create a tissue aspirate). Where appropriate, the kit optionally can contain reaction vessels, mixing vessels, and other components that facilitate the preparation of reagents or the test sample. The kit can also include one or more sample collection/acquisition instruments for assisting with obtaining a test sample, such as various blood collection/transfer devices (e.g., microsampling devices, micro-needles, or other minimally invasive pain-free blood collection methods; blood collection tube(s); lancets; capillary blood collection tubes; other single fingertip-prick blood collection methods; buccal swabs, nasal/throat swabs; 16-gauge or other size needle, circular blade for punch biopsy (e.g., 1-8 mm, or other appropriate size), surgical knife or laser (e.g., particularly hand-held), syringes, sterile container, or canula, for obtaining, storing or aspirating tissue samples; or the like). The kit can include one or more instruments for assisting with joint aspiration, cone biopsies, punch biopsies, fine-needle aspiration biopsies, image-guided percutaneous needle aspiration biopsy, bronchoaveolar lavage, endoscopic biopsies, and laproscopic biopsies.

The following examples further illustrate the invention but, of course, should not be construed as in any way limiting its scope.

Example 1

This example demonstrates a method of analyzing an analyte of interest in a biological sample as disclosed herein.

It has been shown that a single conventional fluorophore (e.g. fluorescein, rhodamime, etc.) can be detected on a low background surface (e.g., specially treated glass or some polymers) using a total internal reflection fluorescence (TIRF) microscope (Skinner, J. P. and S. Y. Tetin, *Microsc Res Tech.*, 78(4): 309-16 (2015)). However, it is difficult to detect a single conventional fluorophore on a microparticle with a conventional fluorescence microscope due to sensitivity issues and fluorescence background of the microparticles. Thus, detecting a single analyte molecule captured by a microparticle with a fluorescent conjugate requires bright signal-generating molecules (e.g., at least 5 times brighter than background fluorescence). As an alternative to nanospheres, streptavidin-phycoerythrin (SAPE) was tested. Phycoerythrin (PE) is known as the brightest fluorescent protein, (e.g. a single PE has the brightness of 20 Cy3 dye molecules). However, while the brightness of PE is on the same order as the background fluorescence of a microparticle, it was difficult to detect captured single analyte molecules. Therefore, SAPE clusters (ProZyme, CA (PJRS34)) were used for single analyte molecule detection on microparticles. Each SAPE cluster contains multiple streptavidin and PE molecules. Dextran-SAPE clusters were generated in-house. When tested in a simple system, biotin-coated microparticles reacted with SAPE clusters, and individual SAPE clusters were detected on microparticles and analyzed in digital mode with LOD as low as 150 aM, as shown in Table 1 (Biophysical Journal, Vol. 112, Issue 3, p295a (2017)).

TABLE 1

| SAPE luster concentration (fM) | Peaks per Area (PPA) |
| --- | --- |
| 12 | 0.26 |
| 4 | 0.08 |
| 1.33 | 0.02 |
| 0.44 | 0.0081 |
| 0.15 | 0.004 |
| 0.05 | 0.0008 |
| 0 | 0 |

However, when tested in other assay systems, the non-specific binding (NSB) of SAPE clusters overwhelmed the specific signal from the bound analyte. Table 2 shows the average pixel intensity on microparticles at various concentration of SAPE clusters in the absence of analyte and/or detection antibody. Average pixel intensity is expressed as counts per pixel (CPP).

TABLE 2

| Microparticles reacted with SAPE cluster (PJRS34) | Average pixel intensity (CPP) |
| --- | --- |
| 380 pM SAPE cluster | 35294 |
| 190 pM SAPE cluster | 33529 |
| 95 pM SAPE cluster | 26719 |
| Buffer only | 0 |

Alternatively, when non-clustered SAPE was used (1:1 cross linked, PJR39S, Prozyme Inc), the NSB was low, as shown in Table 3.

TABLE 3

| Microparticles reacted with monomer SAPE (PJR39S) | CPP |
| --- | --- |
| 800 pM SAPE | <50 |
| Buffer only | 0 |

In summary, a single SAPE cluster (PJRS34) can be detected on microparticles, but caused high non-specific binding and thus, could not be used in immunoassays. In contrast, non-clustered SAPE (PJR39S) did not cause NSB, but its brightness was similar to the microparticle background.

The method described herein provides a solution for direct detecting single analyte molecules on microparticles. Specifically, macroconjugates comprised of dextran cross-linked with multiple BSA molecules, multiple Fabs, and multiple biotin molecules results in low NSB and thus, can be used for single-molecule analyte imaging. On average, each macroconjugate contains one dextran (150 kDa), 15 BSA molecules, 15 Fabs, and 50-100 biotin molecules (schematically depicted in FIG. 1), which can be complexed with multiple non-clustered SAPE molecules. These macroconjugates exhibited low NSB and high binding efficiency and allowed for ultra-sensitive single-molecule analyte detection, as exemplified further below.

Example 2

This example describes an immunoassay to detect HCV antigen in accordance with the methods described herein.

Microparticles and HCV calibrator from on-market kits (HCV core Ag kit, Ref 6L47-29, and HCV Calibrator set, Ref 6L47-02, respectively, Abbott Laboratories, Abbott Park, IL) were diluted with negative human plasma (NHP). Dextran BSA-biotin-Fab clusters were prepared as shown in FIG. 1. Streptavidin phycoerythrin (SAPE, PJR39S) was purchased from Prozyme (Hayward, CA).

The assay was performed in three steps:

Step 1: 100 μL of the HCV calibrators ranging from 0-20000 fM were first mixed with microparticles. Microparticles were incubated at 37° C. and then washed.

Step 2: 100 μL Dextran BSA-biotin-Fab clusters were added to microparticles. Microparticles were incubated and then washed.

Step 3: 100 μL SA-PE was added. Microparticles were incubated, washed, and then imaged on a microscope.

Figure 2:
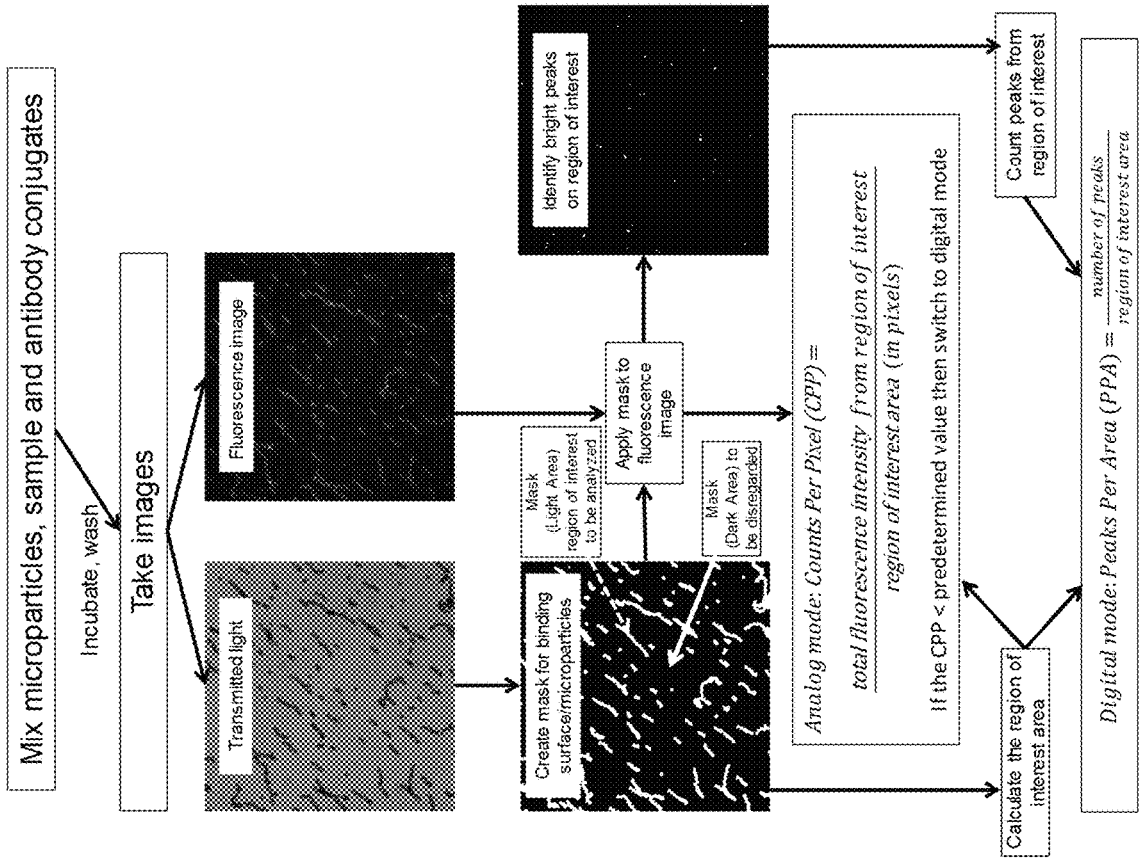
FIG. 2 is a diagram illustrating the analysis of transmitted light and fluorescent images of binding surfaces (e.g., microparticles) as described herein. The transmitted light image is used to locate the region of interest and to determine the region of interest area (or total area). The fluorescence image is used to determine (i) total fluorescence from the region of interest, and/or (ii) the number of bright peaks located on the region of interest. Analog and digital mode results are calculated from these data.

Imaging and analysis: For each sample, 4-9 sets of images were taken with an EM-CCD camera on the inverted Olympus IX83 fluorescence microscope. Each image set consists of a transmitted light image and a fluorescence image corresponding to the color of the fluorophore. Image analysis is schematically depicted in FIG. 2. Images from each sample were simultaneously analyzed in both digital mode and analog mode using a preset value (see Table 4). In this example, the preset (or "predetermined") value was 1000 (depending on the instrument/camera). Therefore, with calibrators less than 40 fM (i.e., signals<1000), the "PPA" value should be used, thus measuring in digital mode; with calibrators greater than 40 fM, "average pixel intensity" value should be used, thus measuring in analog mode. Although the preset value in this example was 1000, one skilled in the art would recognize that the preset value could be lower or higher than 1000 depending on the instrument/camera and reaction conditions.

TABLE 4

| HCV Ag | Analog mode | | Digital mode | |
|---|---|---|---|---|
| (fM) | CPP | SD | PPA | SD |
| 0 | 826 | 54 | 0.0083 | 0.001 |
| 1 | 835 | 49 | 0.049 | 0.01 |
| 3 | 807 | 10 | 0.086 | 0.005 |
| 10 | 849 | 18 | 0.16 | 0.03 |
| 40 | 1085 | 18 | 0.33 | 0.02 |

TABLE 4-continued

| HCV Ag | Analog mode | | Digital mode | |
|---|---|---|---|---|
| (fM) | CPP | SD | PPA | SD |
| 80 | 2088 | 1 | | |
| 600 | 10577 | 558 | | |

Figure 3A:
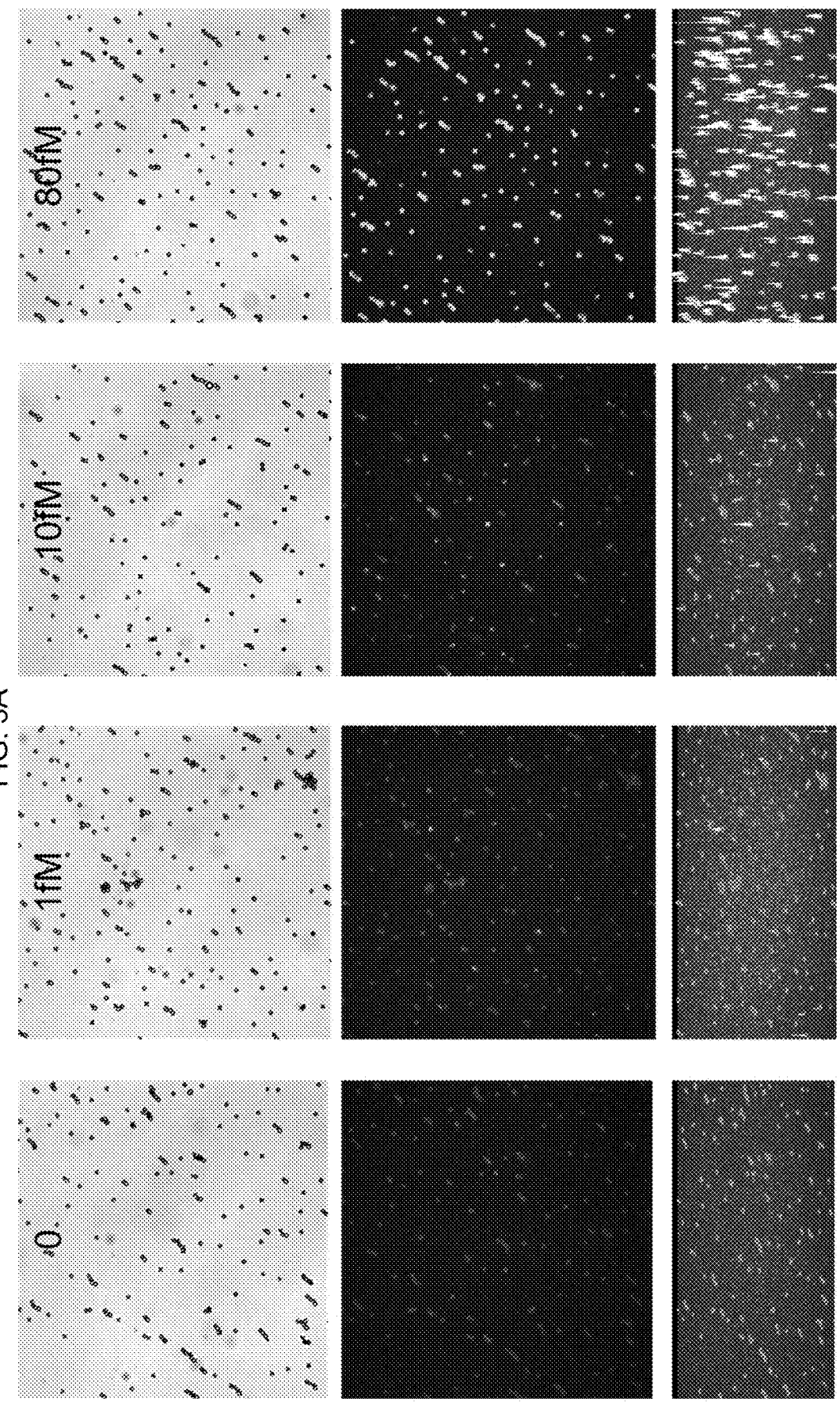
FIG. 3A is a series of transmitted light images (top panels), fluorescent images (center panels), and intensity profiles of the fluorescent images (bottom panels) acquired from the HCV core antigen detection assay (HCV at 0-80 fM) described in Example 2.
Figure 3B:
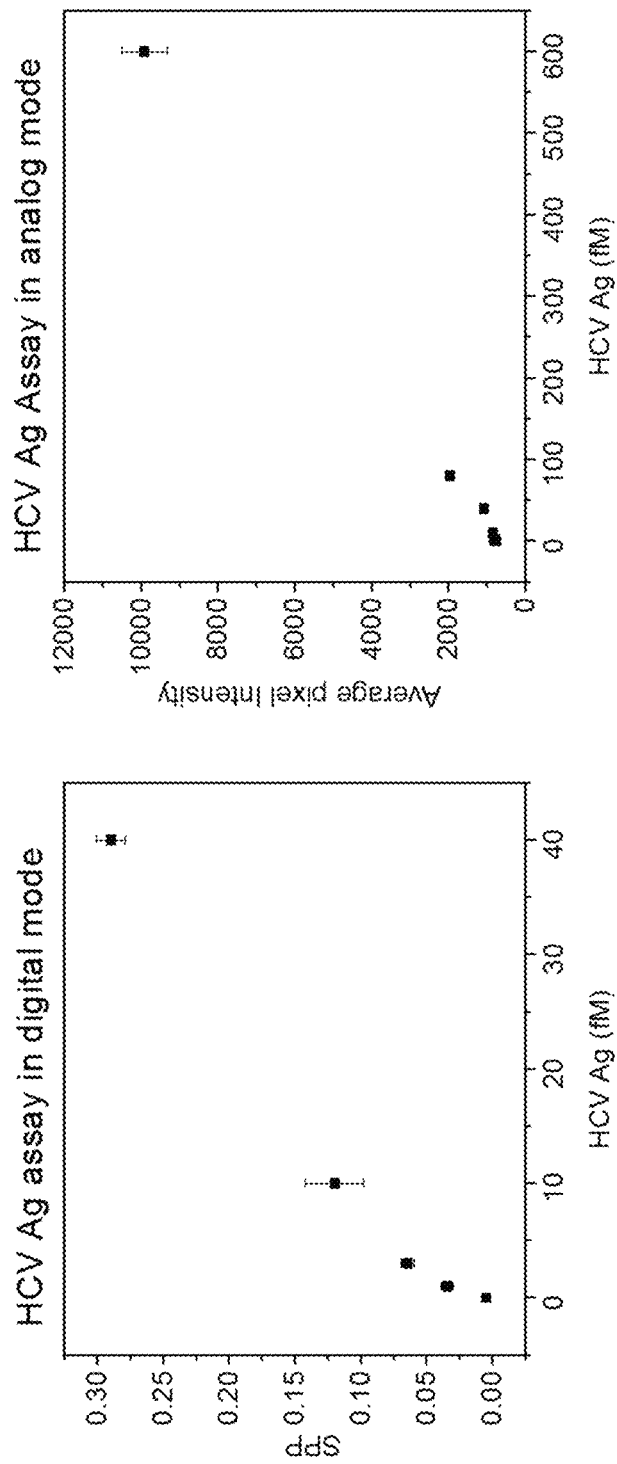
FIG. 3B are graphs of the calibration curves for the HCV assay in the analog mode (left) and the digital mode (right).

FIG. 3A shows examples of the assay images at 0, 1 fM, 10 fM and 80 fM of HCV, as well as the intensity profile of the fluorescence images. At low analyte concentration (e.g. <40 fM), either zero or one immunosandwich complex most likely forms on each microparticle, and individual fluorescence intensity peak can be directly counted using a fixed intensity threshold. The results show that at low analyte concentration (<40 fM), the CPP was within 3 standard deviations (SD) of the negative control. In contrast, in digital mode, 1 fM was easily distinguishable from the negative control. Calibration curves (both digital and analog modes) for this assay are shown in FIG. 3B.

The above-described assay also was performed using an alternative conjugate, Dextran-BSA-PE-Fab, which allows for combination of step 2 and step 3, the results of which are shown in Table 5.

TABLE 5

| HCV Ag | Analog mode | Digital mode |
|---|---|---|
| 0 | 646 | 0.0040 |
| 80 fM | 691 | 0.05 |
| 600 fM | 945 | 0.37 |

Example 3

This example describes an immunoassay to detect HIV in accordance with the methods described herein.

Microparticles used in the assay were coated using an Abbott in-house antibody via EDAC chemistry, and calibrators were prepared from an on-market kit (HIV kit, 25258L100, 65 pg/ml, Abbott Laboratories, Abbott Park, IL) and further diluted with negative human plasma (NHP). Dextran BSA-biotin-Fab clusters were prepared. Streptavidin phycoerythrin (SAPE) was purchased from Prozyme (Hayward, CA).

The assay was performed in two steps:

Step 1: 100 μL of the HIV sample ranging from 0-6.5 pg/ml were first mixed with microparticles, assay specific diluent, and Dextran BSA-biotin-Fab clusters, and microparticles were washed after a 10-minute incubation at 37° C.

Step 2: 100 μL SAPE was added, microparticles were washed after incubation and then imaged on a microscope with an EM-CCD camera.

Imaging acquisition and analysis were carried out as described in Example 2. Analyzing the images in digital mode greatly improved the assay S/N ratio, as shown in Table 6 and FIGS. 4A-4B.

TABLE 6

| pg/ml | Digital mode | Analog mode |
|---|---|---|
| 0.00 | 0.006 | 852 |
| 0.24 | 0.04 | 855 |
| 0.72 | 0.1 | 888 |

TABLE 6-continued

| pg/ml | Digital mode | Analog mode |
|---|---|---|
| 2.17 | 0.24 | 934 |
| 6.50 | 0.35 | 1004 |

SA-APC (Prozyme, Hayward, CA) was used as an alternative fluorescent agent. The immunoassay and image analysis were performed as described in Example 2. The results are shown in Table 7 and FIG. 5.

TABLE 7

| HIV (pg/ml) | Digital mode | Analog mode |
|---|---|---|
| 0.00 | 0.01 | 249 |
| 0.24 | 0.03 | 248 |
| 0.72 | 0.07 | 249 |
| 2.17 | 0.18 | 256 |
| 6.50 | 0.37 | 273 |

Example 4

This example demonstrates that the methods described in Example 3 are also capable of detecting high concentrations of HIV antigen when images were analyzed entirely in analog mode.

Microparticles used in the assay were coated using an Abbott in-house antibody via EDAC chemistry. Analyte panels (2000 pg/ml-4.7 pg/ml) were prepared from a patient sample with high P24 value and serially diluted with negative human plasma (NHP). Dextran BSA-biotin-Fab clusters were prepared. Streptavidin phycoerythrin (SAPE) was purchased from Prozyme (Hayward, CA).

The assay was performed in two steps:

Step 1: 100 µL of each HIV sample were first mixed with microparticles, assay specific diluent, and Dextran BSA-biotin-Fab clusters. Following a 10-minute incubation at 37° C., microparticles were washed.

Step 2: 100 µL SAPE was added, microparticles were washed after a 5-minute incubation and then imaged on a microscope with a PCO sCMOS camera.

Figure 6:
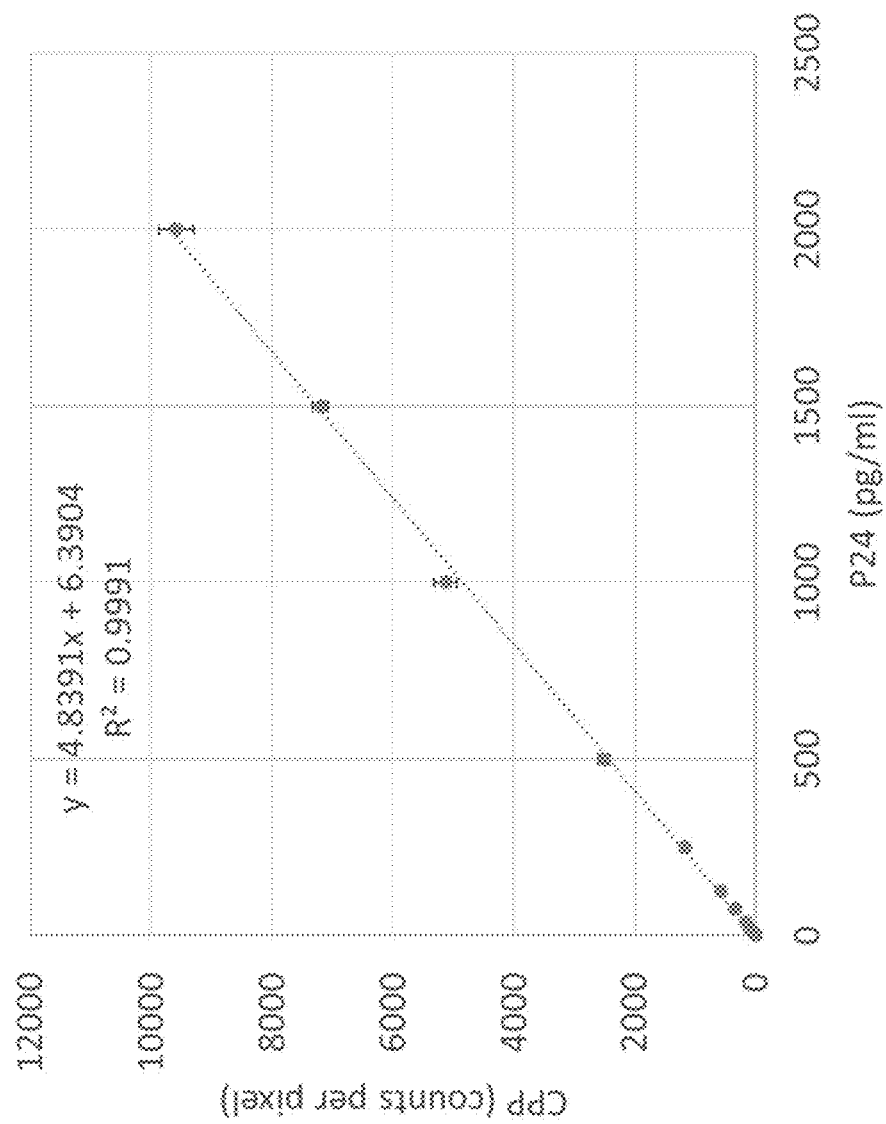
FIG. 6 is a graph illustrating image analysis in analog mode for an HIV P24 assay.

Imaging acquisition and analysis were carried as described in Example 2 except analog mode was used for analysis due to the relatively high analyte concentration (see FIG. 6 and Table 8).

TABLE 8

| P24 (pg/ml) | CPP | SD | CV |
|---|---|---|---|
| 2000 | 9585 | 285.0 | 3% |
| 1500 | 7199 | 128.9 | 2% |
| 1000 | 5127 | 185.5 | 4% |
| 500 | 2503 | 103.4 | 4% |
| 250 | 1166 | 72.8 | 6% |
| 125 | 577 | 30.5 | 4% |
| 75 | 344 | 8.94 | 2% |
| 38 | 166 | 8.07 | 3% |
| 18.8 | 79 | 2.09 | 1% |
| 9.4 | 30 | 3.67 | 2% |
| 4.7 | 13 | 0.42 | 0% |
| 0.0 | 0 | 0.92 | 1% |

Example 5

This example describes an immunoassay method capable of detecting thyroid stimulating hormone (TSH) over a wide concentration range and combining signal from digital mode and analog mode into a single composite signal.

Microparticles used in the assay were coated using an Abbott in-house antibody via EDAC chemistry, analyte panels (100 mIU/L-0.0001 mIU/L, or 715 pM-0.0007 pM) were prepared from a patient sample with high TSH value and serial diluted with assay specific diluent. Dextran BSA-biotin-Fab clusters were prepared. Streptavidin phycoerythrin (SAPE) was purchased from Prozyme (Hayward, CA).

The assay was performed in three steps:

Step 1: 150 µL of each TSH sample were first mixed with microparticles; microparticles were washed after 10 minutes of 37° C. incubation.

Step 2: 80 µL of Dextran BSA-biotin-Fab macroconjugate was added; microparticles were washed after 5 minutes incubation.

Step 3: 80 µL SAPE was added, microparticles were washed after 5 minutes incubation and then imaged on a microscope with a PCO sCMOS camera. Two different exposure times (10 ms and 100 ms) were used for fluorescence images to extend the dynamic range.

Figure 7:
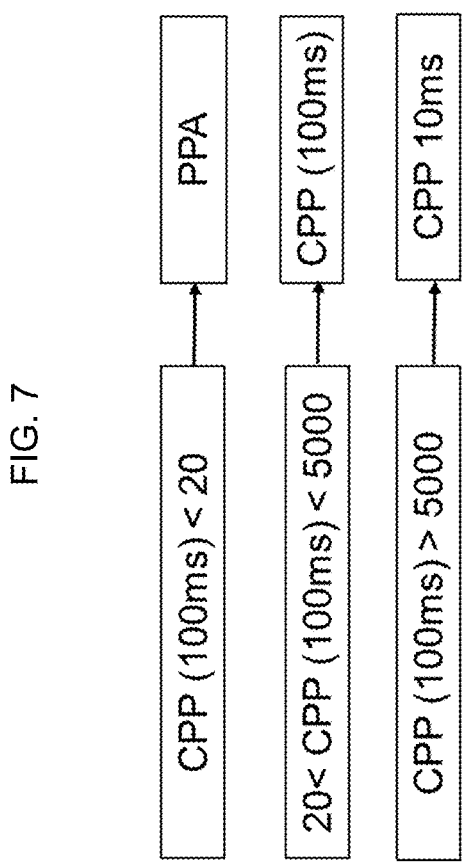
FIG. 7 is a schematic diagram showing the criteria for combining a signal from digital mode and a signal from analog mode into a single composite signal.

Table 8 shows the initial data produced by imaging analysis software and final composite signal after processing. There are three signal values for each sample (PPA, CPP 100 ms, CPP 10 ms) from initial data. Only one signal value will best reflect each sample concentration. The criteria are set as shown in FIG. 7.

Once the appropriate signal value is selected, the corresponding conversion factor is used to calculate composite signal. The conversion factor is calculated by using a sample concentration with a CPP (100 ms) value close to either 5000 or 20. These conversion factors are assay specific and should be set when generating calibration curves. In this example, at 0.781 mIU/L of TSH, the CPP (100 ms) is "5880" and CPP (10 ms) is "694", therefore the conversion factor is 8.47. In another example, at 0.003 mIU/L, the PPA is "0.1886" and CPP is "19", therefore the conversion factor is 100.74.

Examples of building a composite calibration curve:

At 25 mIU/L, the CPP (100 ms) signal is "15064", which is greater than 5000, therefore the signal value "9000" from CPP (10 ms) is used, the final composite signal is: 9000×8.47=76230

At 0.195 mIU/L, the CPP (100 ms) is "1413", which is between 20 and 5000, therefore the signal value "1413" from CPP (100 ms) is used, the final composite signal is: 1413×1=1413

At 0.00076 mIU/L, the CPP (100 ms) is "10", which is less than 20, therefore the signal value "0.0504" from PPA is used, the final composite signal is: 0.0504× 100=5

TABLE 9

Original TSH assay data produced by imaging analysis software and final composite signal after processing. The bolded signals are used to build the composite signal, based on the value selection criteria and conversion factor.

| mIU/L | PPA | CPP (100 ms) | CPP (10 ms) | Conversion factor | Composite signal |
|---|---|---|---|---|---|
| 100 | 0.0422 | 8472 | 12758 | 8.47 | 108063 |
| 50 | 0.1460 | 8606 | 11993 | 8.47 | 101584 |
| 25 | 0.0687 | 15064 | 9000 | 8.47 | 76230 |
| 12.5 | 0.0374 | 26265 | 6267 | 8.47 | 53081 |
| 6.25 | 0.0081 | 29822 | 4047 | 8.47 | 34278 |
| 3.125 | 0.0109 | 18617 | 2358 | 8.47 | 19973 |
| 1.562 | 0.0210 | 10653 | 1281 | 8.47 | 10854 |

TABLE 9-continued

Original TSH assay data produced by imaging analysis software and final composite signal after processing. The bolded signals are used to build the composite signal, based on the value selection criteria and conversion factor.

| mIU/L | PPA | CPP (100 ms) | CPP (10 ms) | Conversion factor | Composite signal |
|---|---|---|---|---|---|
| 0.781 | 0.0357 | 5880 | 694 | 8.47 | 5880 |
| 0.390 | 0.1687 | 2956 | 344 | 1 | 2956 |
| 0.195 | 0.5156 | 1431 | 168 | 1 | 1431 |
| 0.0976 | 0.2723 | 701 | 81 | 1 | 701 |
| 0.0488 | 0.0408 | 352 | 41 | 1 | 352 |
| 0.0244 | 0.4983 | 163 | 19 | 1 | 163 |
| 0.0122 | 0.9575 | 84 | 10 | 1 | 84 |
| 0.0061 | 0.5046 | 41 | 5 | 1 | 41 |
| 0.0030 | 0.1886 | 19 | 2 | 100 | 19 |
| 0.0015 | 0.0890 | 12 | 1 | 100 | 8.9 |
| 0.00076 | 0.0504 | 10 | 1 | 100 | 5 |
| 0.00038 | 0.0244 | 3 | 0 | 100 | 2.4 |
| 0.00019 | 0.0167 | 4 | 0 | 100 | 1.7 |
| 9.53E−05 | 0.0079 | 1 | 0 | 100 | 0.8 |
| 4.7E−05 | 0.0055 | 1 | 0 | 100 | 0.5 |
| 2.4E−05 | 0.0041 | 1 | 0 | 100 | 0.4 |
| 0 | 0.0046 | 0 | 0 | 100 | 0.5 |

The results of this example demonstrate that the model TSH assay is capable of linear TSH detection ranging from 0.00019 mIU/L to 12 mIU/L, which corresponds to a linear dynamic range of 100 pM-1 fM (5 orders of magnitude).

Example 6

This example describes an immunoassay to detect estradiol in accordance with the methods described herein.

Microparticles used in the assay were coated using an Abbott in-house antibody via EDAC chemistry. The assay was performed in three steps:

Step 1: 100 µL of each estradiol calibrator was mixed with microparticles and incubated at for 10 minutes at 37° C. The microparticles were washed after incubation.

Step 2: 80 µL of estradiol-biotin was added; microparticles were washed after 5 minutes incubation.

Step 3: 100 µL SAPE was added and incubated for 5 minutes, microparticles were washed after incubation and then imaged on a microscope with a sCMOS camera.

Figure 8:
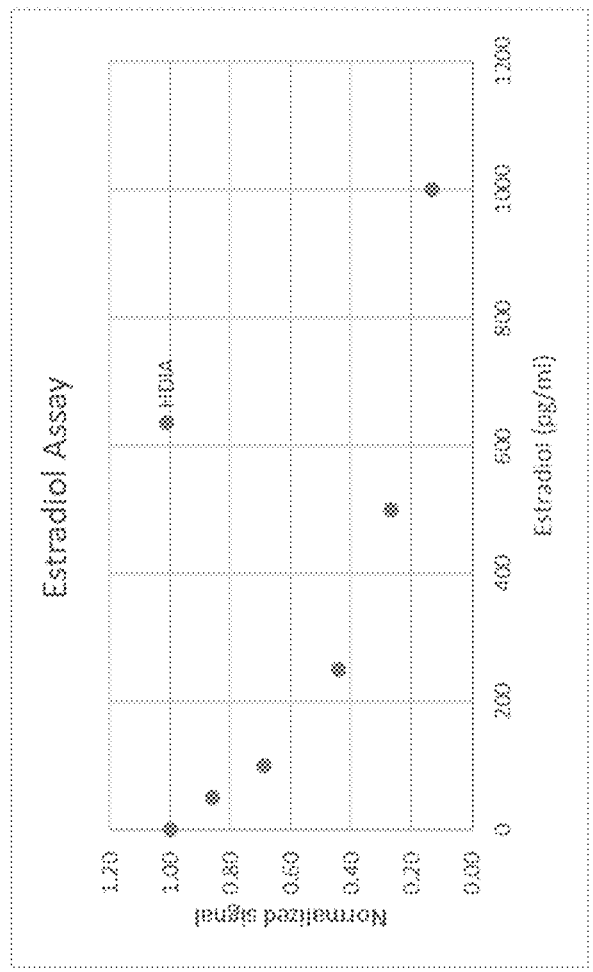
FIG. 8 is a graph illustrating results of the estradiol detection assay described in Example 6.

Imaging acquisition and analysis were carried out as shown in FIG. 2 using the analog mode only. The results of the assay are shown in FIG. 8.

Example 7

This example describes a multiplex immunoassay to detect HCV and HIV antibodies in a sample.

Two types of microparticles were used in this assay: streptavidin coated microparticles and gp41 coated microparticles. The microparticles were reacted with an HCV reagent and an HIV reagent. The HCV reagent contained a mixture of biotin-labeled HCV NS3 antigen and Cy3-labeled NS3 antigen. The HIV reagent contained a mixture of Cy5-labeled HIV peptides and AlexaFluro405-biotin.

The assay was run on an automated instrument (KING-FISHER™) with steps set forth in Table 10.

TABLE 10

| Step 1 | Bind 20 minutes | 100 µl sample, 5 µl MP (2 MPs total 0.1%) + 5 µl HCV reagent. |
| Step 2 | Wash (one time) | 1 minute (200 µl wash buffer) |
| Step 3 | Bind 20 minutes | 100 µl HIV reagent |
| Step 4 | Wash (5 times) | 1 minute (200 µl wash buffer) |

Figure 11:
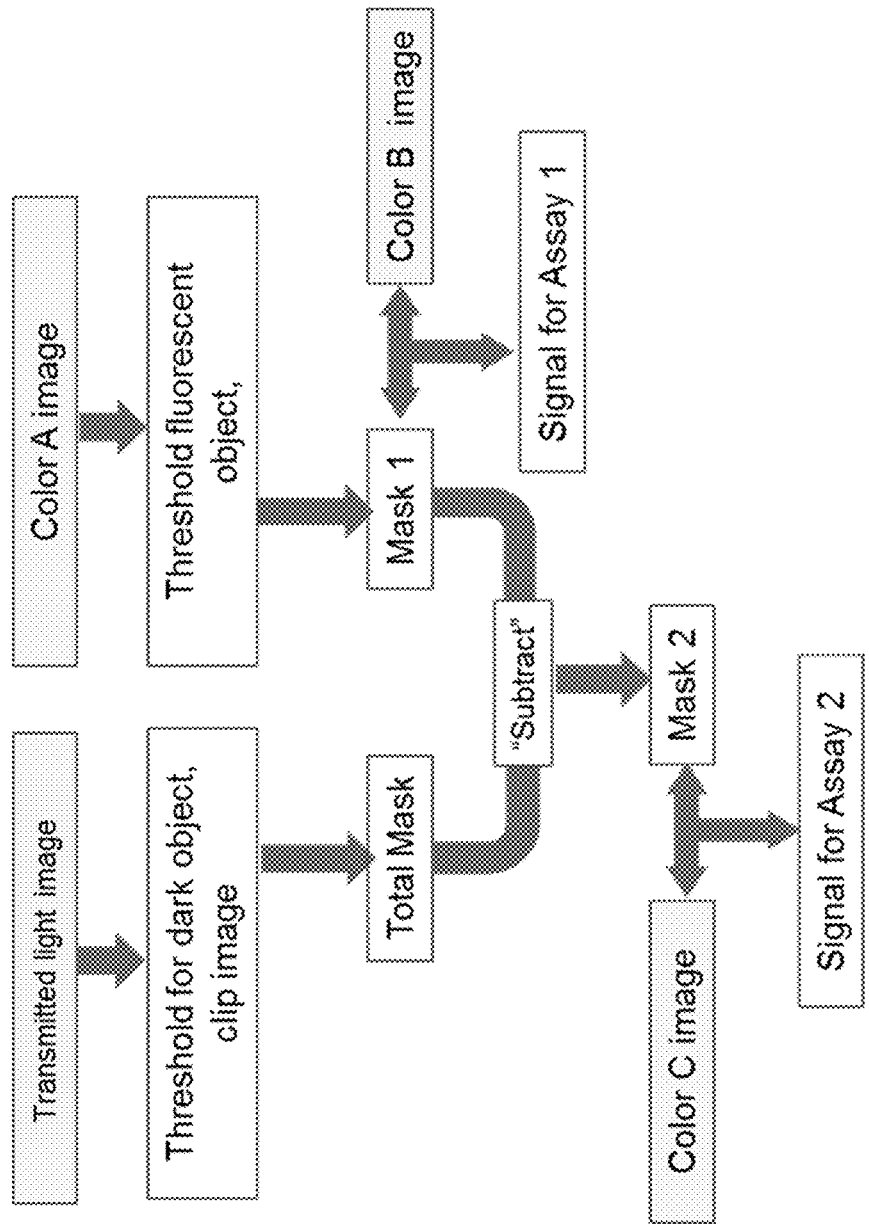
FIG. 11 is a diagram illustrating the sequence of image analyses as described in Example 7.
Figure 12:
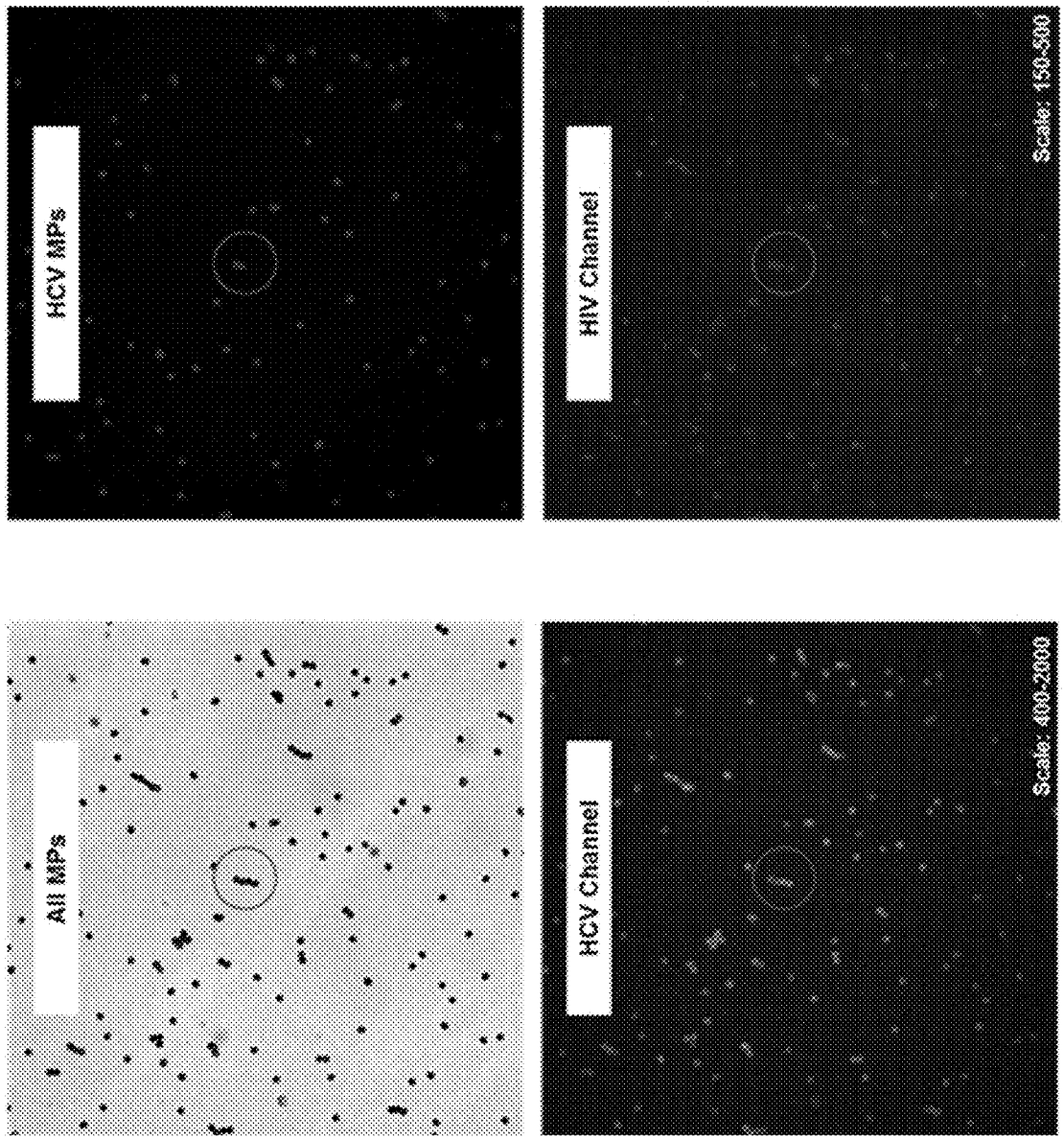
FIG. 12 is a series of images illustrating the results of the immunoassay described in Example 7 for an HCV/HIV-negative sample. The top left panel is a transmitted light image of all microparticles; the top right panel is a fluorescent image corresponding to microparticles stained with color A (HCV MPs); the bottom left panel is a fluorescent image corresponding to signal from MP1 (HCV MPs, color B, dim due to negative sample); the bottom right panel is a fluorescent image corresponding to signal from MP2 (HIV MPs, color C, dim due to negative sample).
Figure 13:
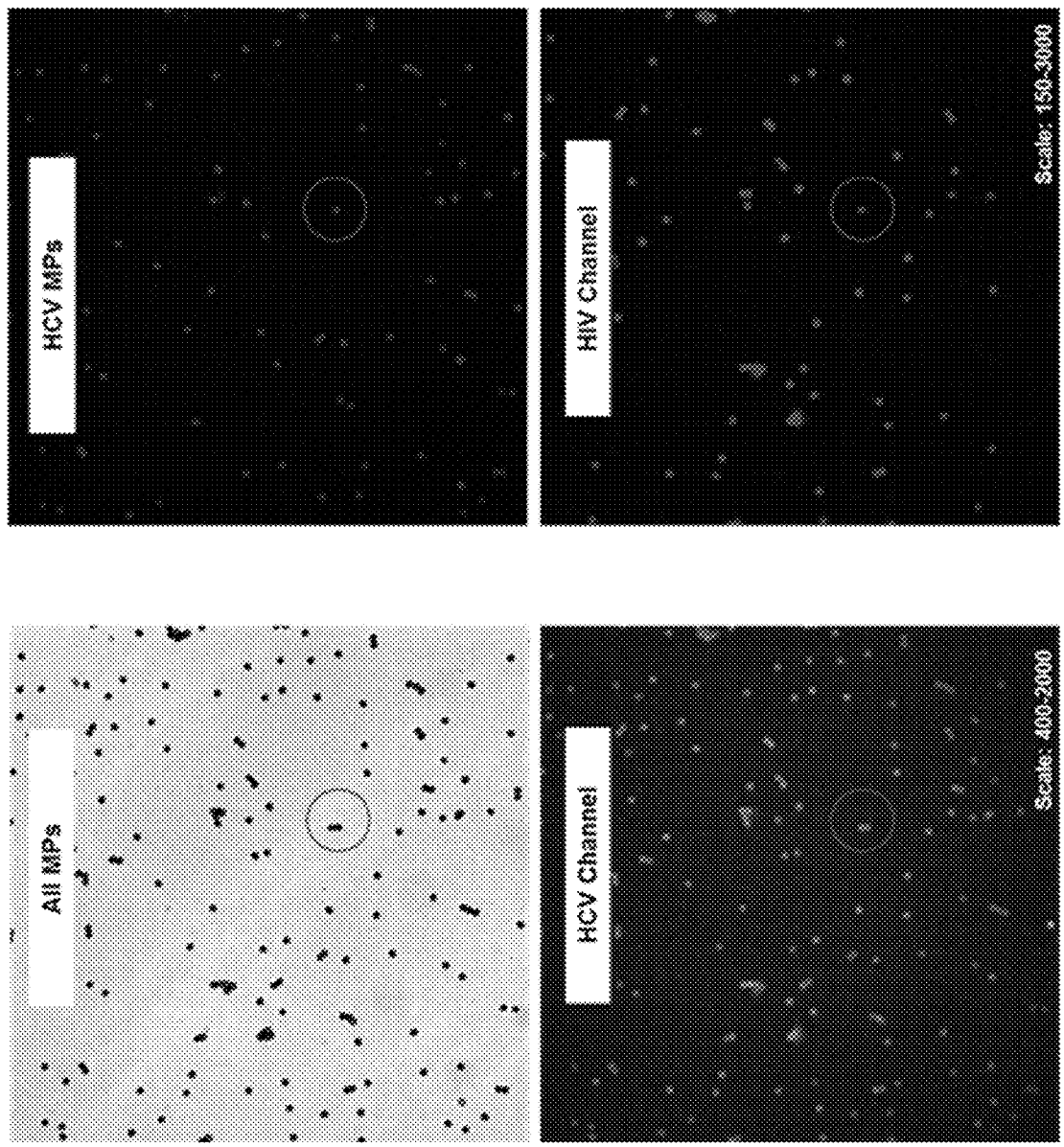
FIG. 13 is a series of images illustrating the results of the immunoassay described in Example 7 for an HIV positive sample. The top left panel is a transmitted light image of all microparticles; the top right panel is a fluorescent image corresponding to microparticles stained with color A (HCV MPs); the bottom left panel is a fluorescent image corresponding to signal from MP1 (HCV MPs, color B, dim due to negative sample); the bottom right panel is a fluorescent image corresponding to signal from MP2 (HIV MPs, color C, bright due to positive sample).
Figure 14:
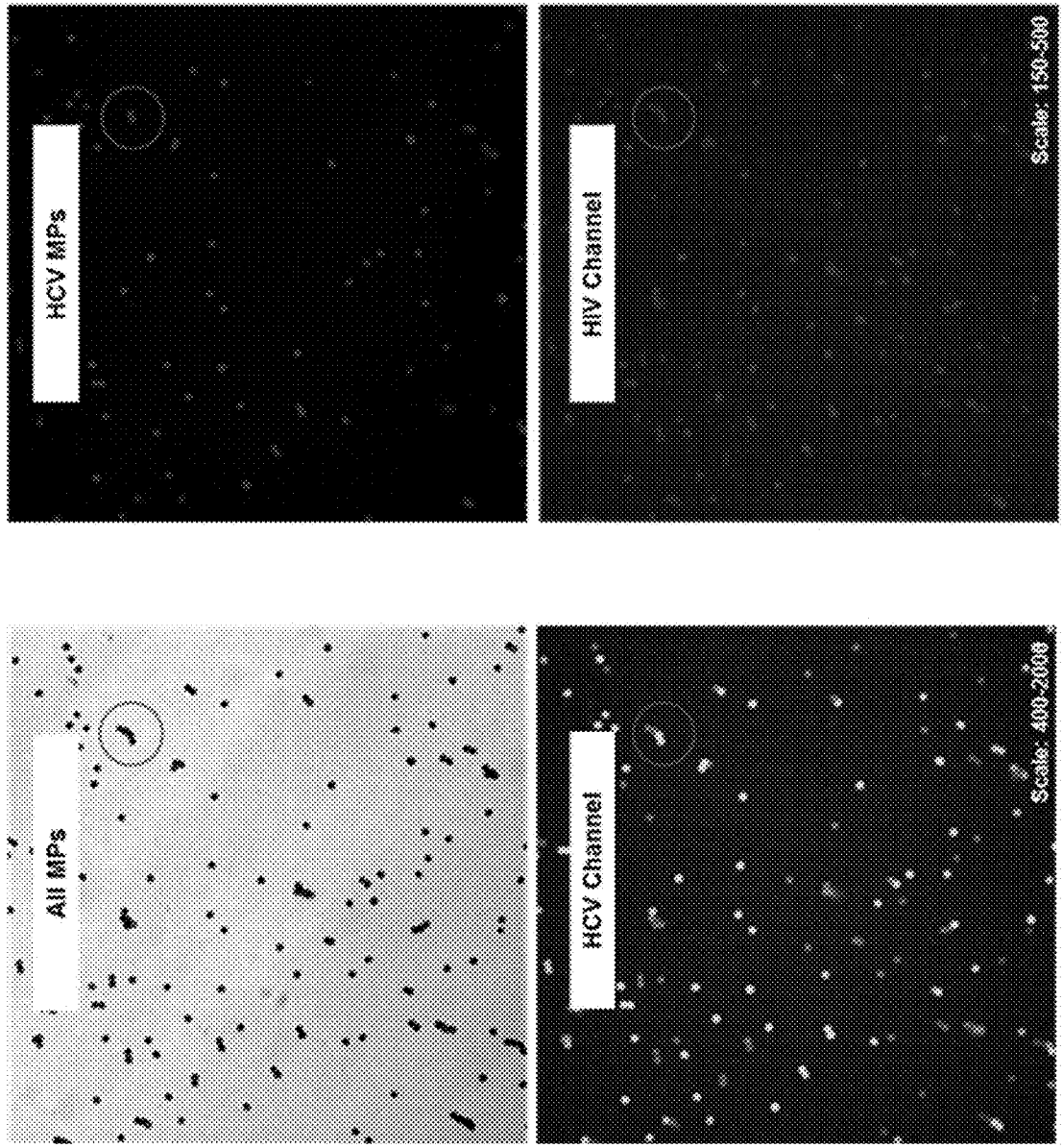
FIG. 14 is a series of images illustrating the results of the immunoassay described in Example 7 for an HCV positive sample. The top left panel is a transmitted light image of all microparticles; the top right panel is a fluorescent image corresponding to microparticles stained with color A (HCV MPs); the bottom left panel is a fluorescent image corresponding to signal from MP1 (HCV MPs, color B, bright due to positive sample); the bottom right panel is a fluorescent image corresponding to signal from MP2 (HIV MPs, color C, dim due to negative sample).

After the reaction, nine sets of images were acquired for each sample and analyzed according to the diagram set forth in FIG. 11. Each set of images included one transmitted light image and three fluorescence images. Assay results for an HCV/HIV-negative sample, an HIV positive sample, and an HCV positive sample are shown in FIGS. 12, 13, and 14, respectively. Table 11 shows the signals for simultaneous detection of HIV and HCV from a single assay run. Sensitivity was equivalent to ARCHITECT® assays.

TABLE 11

|  | HCV Channel | HIV Channel |
|---|---|---|
| Negative Control | 50 | 2 |
| HCV Positive Control | 1130 | 17 |
| HIV Positive Control | 120 | 2085 |

Figure 15:
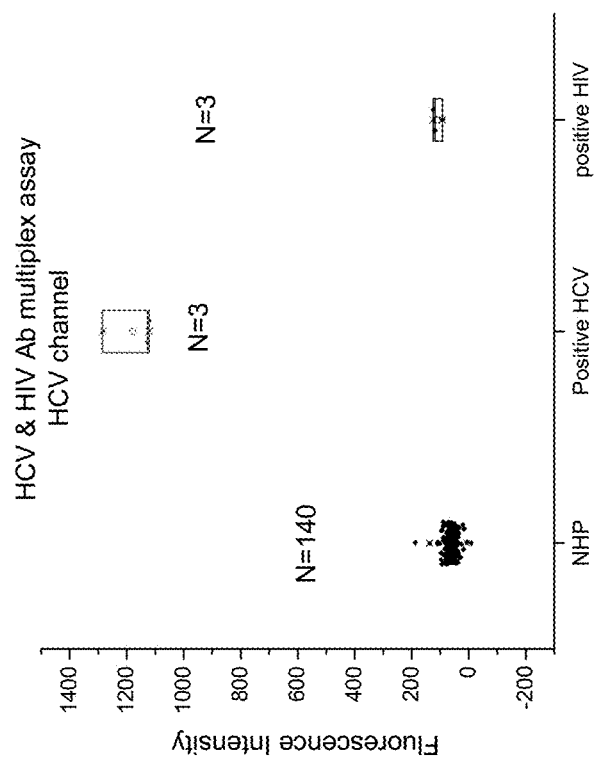
FIG. 15 is a graph illustrating the distribution of 140 normal human samples, positive HCV calibrators, and positive HIV calibrators measured in the HCV channel using the duplex assay format described in Example 7.
Figure 16:
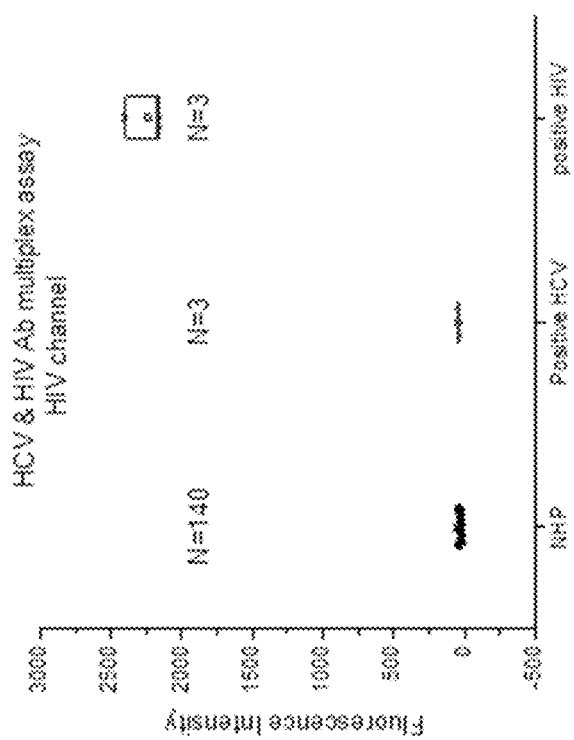
FIG. 16 is a graph illustrating the distribution of 140 normal human samples, positive HCV calibrators, and positive HIV calibrators measured in the HIV channel using the duplex assay format described in Example 7.

Distributions of 140 normal human samples, positive HCV calibrators, and positive HIV calibrators measured using the duplex assay format described above are shown in FIGS. 15 and 16.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

For reasons of completeness, various aspects of the invention are set out in the following numbered clauses:

Clause 1. A method of analyzing an analyte of interest in a biological sample, the method comprising the steps of: (a) capturing an analyte of interest on a binding surface, which binding surface comprises a plurality of specific binding members immobilized thereto that bind to the analyte; (b) reacting a plurality of macroconjugates with the captured analyte; wherein each macroconjugate comprises: (i) a core which comprises a cross-linked protein or polymer comprising a polysaccharide, a dendrimer, a polyether compound, or nanoparticle; (ii) a plurality of specific binding members, fragments thereof, or combinations thereof; (iii) a plurality of tags or detectable labels, wherein when the macroconjugate comprises a plurality of tags, the method comprises reacting a plurality of fluorescent agents with the tags, wherein each fluorescent agent comprises a molecule which is capable of binding to the tag and a detectable label; and optionally (iv) a plurality of carrier proteins; and (c) imaging the binding surface and analyzing the images.

Clause 2. A method of analyzing an analyte of interest in a biological sample, the method comprising the steps of: (a) capturing an analyte of interest on a binding surface, which binding surface comprises a plurality of specific binding members immobilized thereto that bind to the analyte; (b) reacting a plurality of macroconjugates with the captured analyte; wherein each macroconjugate comprises: (i) a core which comprises a cross-linked protein or polymer comprising a polysaccharide, a dendrimer, a polyether compound, or nanoparticle; (ii) a plurality of carrier proteins covalently attached to locations around the core; (iii) a plurality of specific binding members, fragments thereof, or combinations thereof covalently attached to the carrier proteins; and (iv) a plurality of tags covalently attached to the plurality of carrier proteins or the plurality of specific binding members; (c) reacting a plurality of fluorescent agents with the macroconjugates, wherein each fluorescent agent comprises a molecule which is capable of binding to the tag and a detectable label; and (d) imaging the binding surface and analyzing the images.

Clause 3. The method of clause 1 or clause 2, wherein, as a result of reacting the macroconjugates with a plurality of fluorescent agents, the macroconjugates emit a fluorescent signal that is at least 5 times greater than background fluorescence (e.g., 6 times, 7 times, 8 times, 9 times, 10 times, 15 times, 20 times, 30 times, 40 times, 50 times or greater than background fluorescence).

Clause 4. The method of clause 1 or clause 2, wherein the polysaccharide is a dextran, amino dextran or combinations thereof.

Clause 5. The method of clause 1 or clause 2, wherein the dendrimer is a PAMAM dendrimer or a DNA dendrimer.

Clause 6. The method of clause 1 or clause 2, wherein the polyether compound is polyethylene glycol.

Clause 7. The method of any one of clauses 1-6, wherein the carrier proteins are serum albumin proteins.

Clause 8. The method of clause 7, wherein the serum albumin proteins are bovine serum albumin.

Clause 9. The method of any one of clauses 1-8, wherein the tags comprise biotin.

Clause 10. The method of any one of clauses 1-9, wherein the specific binding members comprise a plurality of antibodies.

Clause 11. The method of any one of clauses 1-9, wherein the fragments of the specific binding members comprise a plurality of antibody fragments.

Clause 12. The method of any one of clauses 1-11, wherein the molecule in the fluorescent agent is streptavidin.

Clause 13. The method of any one of clauses 1-12, wherein the detectable label in the fluorescent agent is phycoerythrin or allophycocyanin.

Clause 14. The method of clause 13, wherein the fluorescent agents comprise streptavidin-phycoerythrin conjugates (SAPE) or streptavidin-allophycocyanin (SAAPC) conjugates.

Clause 15. The method of any one of clauses 1-14, wherein the binding surface is imaged on a flat smooth surface of a solid support.

Clause 16. The method of any of clauses 1-15, wherein imaging the binding surface involves acquiring a transmitted light image of the binding surface and one or more fluorescent images corresponding to the fluorescent agents.

Clause 17. The method of clause 16, wherein analyzing the images further comprises calculating average pixel intensity on the binding surface in the one or more fluorescent images. In some embodiments, if the average pixel intensity in the region of interest is less than a predetermined value, analyzing the images comprises: (i) counting high fluorescence intensity peaks in the region of interest; and (ii) determining the ratio of peaks to the region of interest area in the one or more fluorescent images.

Clause 18. The method of clause 17, wherein the average pixel intensity on the binding surface is compared to a predetermined value.

Clause 19. The method of any one of the preceding clauses, wherein, if the average pixel intensity on the binding surface is less than a predetermined value, analyzing the images comprises: (i) identifying the region of interest area on the binding surface; (ii) counting high fluorescence intensity peaks on the binding surface; (iii) determining the ratio of peaks to the region of interest area in the one or more fluorescent images; and (iv) calculating the composite signal using a conversion factor to combine the data points obtained for different analyte concentrations.

Clause 20. The method of clause 19, wherein if the average pixel intensity on the binding surface is less than the predetermined value, then analyzing the images involves identifying the region of interest area on the binding surface, counting the high intensity peaks on the binding surface, and determining the ratio of peaks to region of interest area in the one or more fluorescent images.

Clause 21. The method of any of clauses 1 to 20, wherein the binding surface comprises one more microparticles.

Clause 22. The method of clause 21, wherein each of the one or more microparticles has a size greater than 1 micron.

Clause 23. A method of analyzing two or more analytes of interest in a biological sample in a single assay, which method comprises: (a) capturing a first analyte of interest on a surface of a first microparticle, wherein the first microparticle (i) comprises a plurality of specific binding members immobilized on the surface thereof which bind to the first analyte and (ii) is labeled with a first fluorophore; (b) capturing a second analyte of interest on a surface of a second microparticle, wherein (i) the first analyte is different from the second analyte, and (ii) the second microparticle comprises a plurality of specific binding members immobilized on the surface thereof which bind to the second analyte; (c) reacting the captured first analyte of interest with a first conjugate, wherein the first conjugate comprises a specific binding member that is labeled with a second fluorophore and binds to the first analyte; (d) reacting the captured second analyte with a second conjugate, wherein the second conjugate comprises a specific binding member that is labeled with a third fluorophore and binds to the second analyte, and wherein the first, second, and third fluorophores are different; (e) obtaining a transmitted light image of the first and second microparticles; (f) obtaining separate fluorescent images of the first and second microparticles corresponding to the first, second, and third fluorophores, respectively; and (g) analyzing the images using a customized image analysis process.

Clause 24. The method of clause 23, wherein each of the first analyte and the second analyte is an antigen or an antibody.

Clause 25. The method of clause 23 or clause 24, wherein the first, second, and third fluorophores are selected from AlexaFluor405, AlexaFluor488, Alexa Fluor546, Cy3, Cy5, phycoerythrin, and allophycocyanin.

Clause 26. The method of any one of clauses 23-25, wherein the microparticles are imaged on a flat smooth surface of a solid support.

Clause 27. The method of any one of clauses 23-26, wherein the customized image analysis process comprises: (i) generating a total image mask based on the transmitted light image; (ii) generating a first image mask based on the fluorescent image corresponding to the first fluorophore; (iii) subtracting the first image mask from the total image mask to generate a second image mask; (iv) calculating the signal emitted from the second fluorophore using the first image mask, whereby the first analyte is detected; and (v) calculating the signal emitted from the third fluorophore using the second image mask, whereby the second analyte is detected.

Clause 28. The method of clause 26, wherein calculating the signal in steps (iv) and (v) comprises calculating average pixel intensity on the microparticles in the fluorescent images corresponding to the second and third fluorophores, respectively.

Clause 29. A method of analyzing two or more analytes of interest in a biological sample in a single assay, which method comprises: (a) capturing a first analyte of interest on a surface of a first microparticle, wherein the first microparticle comprises a plurality of specific binding members immobilized on the surface thereof which bind to the first analyte; (b) capturing a second analyte of interest on a surface of a second microparticle, wherein (i) the first analyte is different from the second analyte, (ii) the second microparticle comprises a plurality of specific binding members immobilized on the surface thereof which bind to the second analyte, and (iii) the first microparticle and the second microparticles differ in size and/or shape; (c) reacting the captured first analyte of interest with a first conjugate, wherein the first conjugate comprises a specific binding member that comprises a first fluorophore and binds to the first analyte; (d) reacting the captured second analyte with a second conjugate, wherein the second conjugate comprises a specific binding member that comprises a second fluorophore and binds to the second analyte, and wherein the first and second fluorophores are different; (e) obtaining a transmitted light image of the first and second microparticles; (f) obtaining separate fluorescent images of the first and second microparticles corresponding to the first and second fluorophores, respectively; and (g) analyzing the images using a customized image analysis process.

Clause 30. The method of any one of clauses 23-29, which further comprises analyzing more than two analytes of interest.

Clause 31. The method of clause 30, which comprises: (a) capturing a third, fourth, or subsequent analyte of interest on a surface of a third, fourth, or subsequent microparticle, wherein (i) each of the third, fourth, and subsequent analytes is different from each other and from the first and second analytes, and (ii) the third, fourth, or subsequent microparticle comprises a plurality of specific binding members immobilized on the surface thereof which bind to the third, fourth, or subsequent analyte; (b) reacting the captured third, fourth, or subsequent analyte with a third, fourth, or subsequent conjugate, wherein the third, fourth, or subsequent conjugate comprises a specific binding member that is labeled with a fourth, fifth, or subsequent fluorophore and binds to the third, fourth, or subsequent analyte, and wherein the fourth, fifth, and subsequent fluorophores are different from each other and from each of the first, second, and third fluorophores; (c) obtaining a transmitted light image of the third, fourth, and subsequent microparticles, (d) obtaining separate fluorescent images of the third, fourth, and subsequent microparticles corresponding to the fourth, fifth, and subsequent fluorophores, respectively, and (e) analyzing the images using a customized image analysis process.

Clause 32. The method of clause 31, wherein each of the third, fourth, or subsequent microparticles is labeled with a different fluorophore and/or is of a different size or shape.

Clause 33. The method of any one of clauses 23-32, wherein each of the first analyte and the second analyte is an antigen or an antibody.

Clause 34. The method of any one of clauses 29-33, wherein the fluorophores are selected from AlexaFluor405, AlexaFluor488, Alexa Fluor546, Cy3, Cy5, phycoerythrin, and allophycocyanin.

Clause 35. The method of any of clauses 23-34, wherein the microparticles have a size greater than 1 micron.

Clause 36. The method of any one of clauses 23-35, wherein each of the first and second analytes is produced by the same organism.

Clause 37. The method of any one of clauses 23-35, wherein each of the first and second analytes is produced by a different organism.

The invention claimed is:

1. A method of analyzing an analyte of interest in a biological sample, the method comprising the steps of:
   a. capturing an analyte of interest on a binding surface, which binding surface comprises a plurality of specific binding members immobilized thereto that bind to the analyte;
   b. reacting a plurality of macroconjugates with the captured analyte; wherein each macroconjugate comprises:
      i. a core which comprises a cross-linked protein or polymer comprising a polysaccharide, a dendrimer, a polyether compound, or nanoparticle;
      ii. a plurality of specific binding members, fragments thereof, or combinations thereof;
      iii. a plurality of tags, wherein the method comprises reacting a plurality of fluorescent agents with the tags, wherein each fluorescent agent comprises a detectable label and a molecule which is capable of binding to the tag;
      iv. a plurality of carrier proteins, wherein: (a) the plurality of carrier proteins are covalently attached to the core; (b) the plurality of tags are covalently attached to the plurality of carrier proteins and (c) the plurality of specific binding members are covalently attached to the plurality of carrier proteins; and c. imaging the binding surface and analyzing the images.

2. The method of claim 1, wherein the polysaccharide is a dextran, amino dextran or combinations thereof.

3. The method of claim 1, wherein the dendrimer is a PAMAM dendrimer or a DNA dendrimer.

4. The method of claim 1, wherein the polyether compound is polyethylene glycol.

5. The method of claim 1, wherein the carrier proteins are serum albumin proteins.

6. The method of claim 5, wherein the serum albumin proteins are bovine serum albumin.

7. The method of claim 1, wherein the tags comprise biotin.

8. The method of claim 1, wherein the specific binding members comprise antibodies.

9. The method of claim 1, wherein the fragments of specific binding members comprise antibody fragments.

10. The method of claim 1, wherein the molecule which is capable of binding to the tag is streptavidin.

11. The method of claim 1, wherein the detectable label in the fluorescent agent is phycoerythrin or allophycocyanin.

12. The method of claim 11, wherein the fluorescent agents comprise streptavidin-phycoerythrin conjugates (SAPE) or streptavidin-allophycocyanin (SAAPC) conjugates.

13. The method of claim 1, wherein the binding surface is imaged on a flat smooth surface of a solid support.

14. The method of claim 1, wherein imaging the binding surface involves acquiring a transmitted light image of the binding surface and one or more fluorescent images corresponding to the fluorescent agents.

15. The method of claim 14, wherein analyzing the images further comprises calculating average pixel intensity on the binding surface in the one or more fluorescent images.

16. The method of claim 15, wherein, if the average pixel intensity in a region of interest is less than a predetermined value, analyzing the images comprises:

(i) counting high fluorescence intensity peaks in the region of interest; and (ii) determining the ratio of peaks to the region of interest area in the one or more fluorescent images.

17. The method of claim 16, further comprising calculating a composite signal using a conversion factor to combine the data points obtained for different analyte concentrations after step (ii).

18. The method of claim 1, wherein the binding surface comprises one or more microparticles.

19. The method of claim 18, wherein each of the one or more microparticles has a size greater than 1 micron.

* * * * *